(12) United States Patent
Yang et al.

(10) Patent No.: US 8,889,430 B2
(45) Date of Patent: Nov. 18, 2014

(54) NANOSTRUCTURES, METHODS OF SYNTHESIZING THEREOF, AND METHODS OF USE THEREOF

(75) Inventors: Lily Yang, Decatur, GA (US); Hui Mao, Alpharetta, GA (US); Shuming Nie, Atlanta, GA (US); Xiaohu Gao, Shoreline, WA (US)

(73) Assignee: Emory University, Atlanta, GA (US)

( * ) Notice: Subject to any disclaimer, the term of this patent is extended or adjusted under 35 U.S.C. 154(b) by 1606 days.

(21) Appl. No.: 12/299,079

(22) PCT Filed: May 4, 2007

(86) PCT No.: PCT/US2007/010894
§ 371 (c)(1),
(2), (4) Date: Jan. 29, 2009

(87) PCT Pub. No.: WO2008/054523
PCT Pub. Date: May 8, 2008

(65) Prior Publication Data
US 2009/0196831 A1  Aug. 6, 2009

Related U.S. Application Data

(60) Provisional application No. 60/797,613, filed on May 4, 2006.

(51) Int. Cl.
| | | |
|---|---|---|
| G01N 33/553 | (2006.01) | |
| A61K 49/18 | (2006.01) | |
| A61K 49/00 | (2006.01) | |
| B82Y 5/00 | (2011.01) | |
| C07K 16/28 | (2006.01) | |
| A61K 39/00 | (2006.01) | |

(52) U.S. Cl.
CPC ......... *C07K 16/2863* (2013.01); *A61K 49/1866* (2013.01); *A61K 49/0032* (2013.01); *A61K 49/0093* (2013.01); *A61K 49/0056* (2013.01); *A61K 49/0058* (2013.01); *B82Y 5/00* (2013.01); *A61K 2039/505* (2013.01); *A61K 49/0034* (2013.01); *C07K 2317/622* (2013.01); *C07K 2317/77* (2013.01)
USPC .............................. 436/526; 436/544; 436/75

(58) Field of Classification Search
CPC ........... C07K 16/2863; C07K 2317/77; C07K 2317/622; G01N 33/532; G01N 33/587; A61K 47/48884; A61K 49/0093; A61K 49/1866; A61K 49/0032; A61K 49/0034; A61K 49/0058
See application file for complete search history.

(56) References Cited

U.S. PATENT DOCUMENTS

| 6,287,857 B1 | 9/2001 | O-riordan | |
|---|---|---|---|
| 7,217,457 B2 * | 5/2007 | Elaissari et al. | .............. 428/407 |

(Continued)

OTHER PUBLICATIONS

Chen X, Conti PS, Moats RA. In vivo near-infrared fluorescence imaging of integrin alphavbeta3 in brain tumor xenografts. Cancer Res 2004;64:8009-14.

(Continued)

*Primary Examiner* — Shafiqul Haq
(74) *Attorney, Agent, or Firm* — Emory Patent Group

(57) ABSTRACT

A nanostructure and methods of synthesizing same. In one embodiment, the nanostructure includes a magnetic iron oxide nanoparticle, a hydrophobic protection structure including at least an amphiphilic copolymer, wherein the hydrophobic protection structure encapsulates the magnetic iron oxide nanoparticle, and at least one amino-terminal fragment (ATF) peptide or epidermal growth factor receptor (EGFR) antibody conjugated to the amphiphilic copolymer.

29 Claims, 12 Drawing Sheets

(56) References Cited

U.S. PATENT DOCUMENTS

| | | | |
|---|---|---|---|
| 7,846,412 B2* | 12/2010 | Nie et al. | 423/414 |
| 2004/0181114 A1* | 9/2004 | Hainfeld et al. | 600/1 |
| 2005/0265922 A1 | 12/2005 | Nie et al. | |

OTHER PUBLICATIONS

Law B, Curino A, Bugge TH, Weissleder R, Tung CH. Design, synthesis, and characterization of urokinase plasminogen-activator-sensitive near-infrared reporter. Chem Biol 2004;11:99-106.

Soltesz EG, Kim S, Laurence RG, DeGrand AM, Parungo CP, Dor DM, Cohn LH, Bawendi MG, Frangioni JV, Mihaljevic T. Intraoperative sentinel lymph node mapping of the lung using near-infrared fluorescent quantum dots. Ann Thorac Surg 2005;79:269-77; discussion 269-77.

Gupta AK, Gupta M. Synthesis and surface engineering of iron oxide nanoparticles for biomedical applications. Biomaterials 2005;26:3995-4021.

Sundstrom JB, Mao H, Santoianni R, Villinger F, Little DM, Huynh TT, Mayne AE, Hao E, Ansari AA. Magnetic resonance imaging of activated proliferating rhesus macaque T cells labeled with superparamagnetic monocrystalline iron oxide nanoparticles. J Acquir Immune Defic Syndr 2004;35:9-21.

Funovics MA, Kapeller B, Hoeller C, Su HS, Kunstfeld R, Puig S, Macfelda K. MR imaging of the her2/neu and 9.2.27 tumor antigens using immunospecific contrast agents. Magn Reson Imaging 2004;22:843-50.

Josephson L, Kircher MF, Mahmood U, Tang Y, Weissleder R. Near-infrared fluorescent nanoparticles as combined MR/optical imaging probes. Bioconjug Chem 2002;13:554-60.

Kobayashi H, Brechbiel MW. Dendrimer-based nanosized MRI contrast agents. Curr Pharm Biotechnol 2004;5:539-49.

Artemov D, Mori N, Okollie B, Bhujwalla ZM. MR molecular imaging of the Her-2/neu receptor in breast cancer cells using targeted iron oxide nanoparticles. Magn Reson Med 2003;49:403-8.

Gao X, Cui Y, Levenson RM, Chung LW, Nie S. In vivo cancer targeting and imaging with semiconductor quantum dots. Nat Biotechnol 2004;22:969-76.

Harisinghani MG, Barentsz J, Hahn PF, Deserno WM, Tabatabaei S, van de Kaa CH, de la Rosette J, Weissleder R. Noninvasive detection of clinically occult lymph-node metastases in prostate cancer. N Engl J Med 2003;348:2491-9.

Hood JD, Bednarski M, Frausto R, Guccione S, Reisfeld RA, Xiang R, Cheresh DA. Tumor regression by targeted gene delivery to the neovasculature. Science 2002;296:2404-7.

Kumar NA, Schnall MD. MR imaging: its current and potential utility in the diagnosis and management of breast cancer. Magn Reson Imaging Clin N Am 2000;8:715-28.

Bombardieri E, Crippa F. PET imaging in breast cancer. Q J Nucl Med 2001;45:245-56.

Romer J, Nielsen BS, Ploug M. The urokinase receptor as a potential target in cancer therapy. Curr Pharm Des 2004;10:2359-76.

Artemov D, Mori N, Ravi R, Bhujwalla ZM. Magnetic resonance molecular imaging of the HER-2/neu receptor. Cancer Res 2003;63:2723-7.

Bander NH, Trabulsi EJ, Kostakoglu L, Yao D, Vallabhajosula S, Smith-Jones P, Joyce MA, Milowsky M, Nanus DM, Goldsmith SJ. Targeting metastatic prostate cancer with radiolabeled monoclonal antibody J591 to the extracellular domain of prostate specific membrane antigen. J Urol 2003;170:1717-21.

Moon WK, Lin Y, O'Loughlin T, Tang Y, Kim DE, Weissleder R, Tung CH. Enhanced tumor detection using a folate receptor-targeted near-infrared fluorochrome conjugate. Bioconjug Chem 2003;14:539-45.

Mahmood U, Weissleder R. Near-infrared optical imaging of proteases in cancer. Mol Cancer Ther 2003;2:489-96.

Schirner M, Menrad A, Stephens A, Frenzel T, Hauff P, Licha K. Molecular imaging of tumor angiogenesis. Ann N Y Acad Sci 2004;1014:67-75.

Brigger I, Dubernet C, Couvreur P. Nanoparticles in cancer therapy and diagnosis. Adv Drug Deliv Rev 2002;54:631-51.

Brannon-Peppas L, Blanchette JO. Nanoparticle and targeted systems for cancer therapy. Adv Drug Deliv Rev 2004;56:1649-59.

Hallahan D, Geng L, Qu S, Scarfone C, Giorgio T, Donnelly E, Gao X, Clanton J. Integrin-mediated targeting of drug delivery to irradiated tumor blood vessels. Cancer Cell 2003;3:63-74.

Jain RK. Delivery of molecular and cellular medicine to solid tumors. Adv Drug Deliv Rev 1997;26:71-90.

Padera TP, Stoll BR, Tooredman JB, Capen D, di Tomaso E, Jain RK. Pathology: cancer cells compress intratumour vessels. Nature 2004;427:695.

Jain RK. Transport of molecules, particles, and cells in solid tumors. Annu Rev Biomed Eng 1999;1:241-63.

Hanahan D, Weinberg RA. The hallmarks of cancer. Cell 2000;100:57-70.

Behrendt N. The urokinase receptor (uPAR) and the uPAR-associated protein (uPARAP/Endo180): membrane proteins engaged in matrix turnover during tissue remodeling. Biol Chem 2004;385:103-36.

Rabbani SA, Mazar AP. The role of the plasminogen activation system in angiogenesis and metastasis. Surg Oncol Clin N Am 2001;10:393-415, x.

Liu D, Aguirre Ghiso J, Estrada Y, Ossowski L. EGFR is a transducer of the urokinase receptor initiated signal that is required for in vivo growth of a human carcinoma. Cancer Cell 2002;1:445-57.

Carriero MV, Del Vecchio S, Capozzoli M, Franco P, Fontana L, Zannetti A, Botti G, D'Aiuto G, Salvatore M, Stoppelli MP. Urokinase receptor interacts with alpha(v)beta5 vitronectin receptor, promoting urokinase-dependent cell migration in breast cancer. Cancer Res 1999;59:5307-14.

Hemsen A, Riethdorf L, Brunner N, Berger J, Ebel S, Thomssen C, Janicke F, Pantel K. Comparative evaluation of urokinase-type plasminogen activator receptor expression in primary breast carcinomas and on metastatic tumor cells. Int J Cancer 2003;107:903-9.

Meijer-van Gelder ME, Look MP, Peters HA, Schmitt M, Brunner N, Harbeck N, Klijn JG, Foekens JA. Urokinase-type plasminogen activator system in breast cancer: association with tamoxifen therapy in recurrent disease. Cancer Res 2004;64:4563-8.

Solberg H, Ploug M, Hoyer-Hansen G, Nielsen BS, Lund LR. The murine receptor for urokinase-type plasminogen activator is primarily expressed in tissues actively undergoing remodeling. J Histochem Cytochem 2001;49:237-46.

Dear AE, Medcalf RL. The urokinase-type-plasminogen-activator receptor (CD87) is a pleiotropic molecule. Eur J Biochem 1998;252:185-93.

Li H, Lu H, Griscelli F, Opolon P, Sun LQ, Ragot T, Legrand Y, Belin D, Soria J, Soria C, Perricaudet M, Yeh P. Adenovirus-mediated delivery of a uPA/uPAR antagonist suppresses angiogenesis-dependent tumor growth and dissemination in mice. Gene Ther 1998;5:1105-13.

Ignar DM, Andrews JL, Witherspoon SM, Leray JD, Clay WC, Kilpatrick K, Onori J, Kost T, Emerson DL. Inhibition of establishment of primary and micrometastatic tumors by a urokinase plasminogen activator receptor antagonist. Clin Exp Metastasis 1998;16:9-20.

Harris RC, Chung E, Coffey RJ. EGF receptor ligands. Exp Cell Res 2003;284:2-13.

Mendelsohn J. Targeting the epidermal growth factor receptor for cancer therapy. J Clin Oncol 2002;20:1S-13S.

Arteaga CL, Baselga J. Tyrosine kinase inhibitors: why does the current process of clinical development not apply to them? Cancer Cell 2004;5:525-31.

Dancey JE. Predictive factors for epidermal growth factor receptor inhibitors—the bull's-eye hits the arrow. Cancer Cell 2004;5:411-5.

Arteaga CL, Truica CI. Challenges in the development of anti-epidermal growth factor receptor therapies in breast cancer. Semin Oncol 2004;31:3-8.

Aziz SA, Pervez S, Khan S, Kayani N, Rahbar MH. Epidermal growth factor receptor (EGFR) as a prognostic marker: an immunohistochemical study on 315 consecutive breast carcinoma patients. J Pak Med Assoc 2002;52:104-10.

(56) References Cited

OTHER PUBLICATIONS

Wikstrand CJ, McLendon RE, Friedman AH, Bigner DD. Cell surface localization and density of the tumor-associated variant of the epidermal growth factor receptor, EGFRvIII. Cancer Res 1997;57:4130-40.

Tsutsui S, Ohno S, Murakami S, Hachitanda Y, Oda S. Prognostic value of epidermal growth factor receptor (EGFR) and its relationship to the estrogen receptor status in 1029 patients with breast cancer. Breast Cancer Res Treat 2002;71:67-75.

Nicholson RI, Gee JM, Harper ME. EGFR and cancer prognosis. Eur J Cancer 2001;37 Suppl 4:S9-15.

Albanell J, Codony J, Rovira A, Mellado B, Gascon P. Mechanism of action of anti-HER2 monoclonal antibodies: scientific update on trastuzumab and 2C4. Adv Exp Med Biol 2003;532:253-68.

Solbach C, Roller M, Ahr A, Loibl S, Nicoletti M, Stegmueller M, Kreysch HG, Knecht R, Kaufmann M. Anti-epidermal growth factor receptor-antibody therapy for treatment of breast cancer. Int J Cancer 2002;101:390-4.

Kim ES, Khuri FR, Herbst RS. Epidermal growth factor receptor biology (IMC-C225). Curr Opin Oncol 2001;13:506-13.

Adams GP, Schier R, McCall AM, Simmons HH, Horak EM, Alpaugh RK, Marks JD, Weiner LM. High affinity restricts the localization and tumor penetration of single-chain fv antibody molecules. Cancer Res 2001;61:4750-5.

Bruell D, Bruns CJ, Yezhelyev M, Huhn M, Muller J, Ischenko I, Fischer R, Finnern R, Jauch KW, Barth S. Recombinant anti-EGFR immunotoxin 425(scFv)-ETA' demonstrates anti-tumor activity against disseminated human pancreatic cancer in nude mice. Int J Mol Med 20051 5:305-13.

Jannot CB, Beerli RR, Mason S, Gullick WJ, Hynes NE. Intracellular expression of a single-chain antibody directed to the EGFR leads to growth inhibition of tumor cells. Oncogene 1996;13:275-82.

Shinkai M, Ito A. Functional magnetic particles for medical application. Adv Biochem Eng Biotechnol 2004;91:191-220.

Bulte JW, Kraitchman DL. Iron oxide MR contrast agents for molecular and cellular imaging. NMR Biomed 2004;17:484-99.

Akerman ME, Chan WC, Laakkonen P, Bhatia SN, Ruoslahti E. Nanocrystal targeting in vivo. Proc Natl Acad Sci U S A 2002;99:12617-21.

Rusckowski M, Qu T, Chang F, Hnatowich DJ. Technetium-99m labeled epidermal growth factor-tumor imaging in mice. J Pept Res 1997;50:393-401.

Gao X, Nie S. Quantum dot-encoded mesoporous beads with high brightness and uniformity: rapid readout using flow cytometry. Anal Chem 2004;76:2406-10.

Bailey RE, Nie S. Alloyed semiconductor quantum dots: tuning the optical properties without changing the particle size. J Am Chem Soc 2003;125:7100-6.

Kim S, Lim YT, Soltesz EG, De Grand AM, Lee J, Nakayama A, Parker JA, Mihaljevic T, Laurence RG, Dor DM, Cohn LH, Bawendi MG, Frangioni JV. Near-infrared fluorescent type II quantum dots for sentinel lymph node mapping. Nat Biotechnol 2004;22:93-7.

\* cited by examiner

A. Detection of uPAR expression by
Immunofluorescence labeling

B. Determination of specificity of recombinant ATF peptides
and ATF-IO nanoparticles using Pull-down assay C. Specific binding and internalization of Cy5.5-ATF-IO
nanoparticles in uPAR expressing tumor cells A. Detection of level of ATF-IO in tumor cells using Prussian blue staining B. T2 Map of MR image of tumor cells A. MR image of a S.C. mammary tumor B. Comparison of T2 intensity changes in mouse received IO or ATF-IO nanparticles C. Prussian blue staining S.C. tumor Lung metastasis Normal tissue

A. Real time NIRF optical imaging of tumor targeting and tissue distribution of Cy5.5-ATF-IO nanoparticles after the tail vein injection.
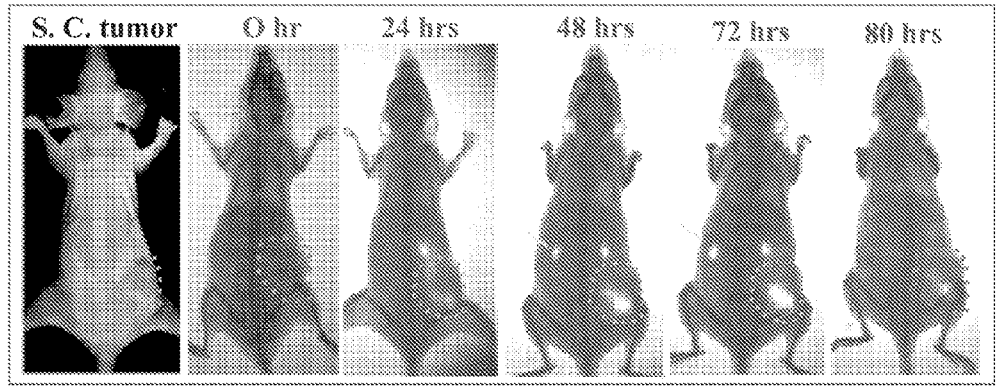
B. MR Imaging of the tumor
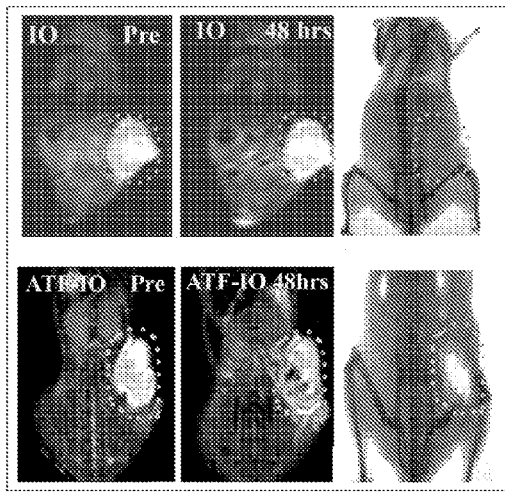
C. Histological analysis of the tumor tissues
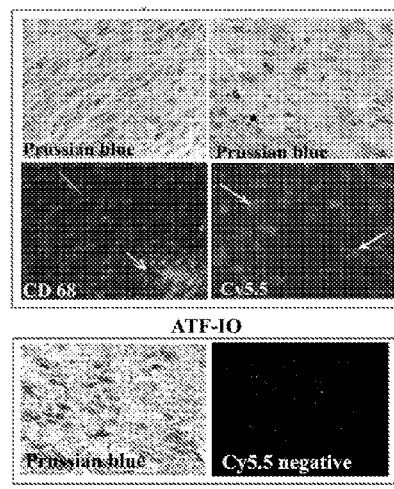
Fig. 7(A-C)

D. T2 map of a series of MR images taken from a s.c. mammary tumor lesion

NANOSTRUCTURES, METHODS OF SYNTHESIZING THEREOF, AND METHODS OF USE THEREOF

CROSS-REFERENCE TO RELATED PATENT APPLICATION

This application claims the benefit, pursuant to 35 U.S.C. §119(e), of U.S. provisional patent application Ser. No. 60/797,613, filed May 4, 2006, entitled "NANOSTRUCTURES, METHODS OF SYNTHESIZING THEREOF, AND METHODS OF USE THEREOF," by Lily Yang et al., which is incorporated herein by reference in its entirety.

This application is related to a copending U.S. patent application entitled "BIOCONJUGATED NANOSTRUCTURES, METHODS OF FABRICATION THEREOF, AND METHODS OF USE THEREOF", U.S. patent application Ser. No. 10/988,923, filed Nov. 15, 2004 with the same assignee as the present invention. The two applicants of the above identified copending applications are also applicants of this application. The disclosure of the above identified copending application is incorporated herein by reference.

This application is also related to a copending PCT international patent application entitled "MULTIFUNCTIONAL NANOSTRUCTURES, METHODS OF SYNTHESIZING THEREOF, AND METHODS OF USE THEREOF", PCT patent application serial No. PCT/US2006/16880, filed May 2, 2006 with the same assignee as the present invention. The three applicants of the above identified copending PCT application are also applicants of this application. The disclosure of the above identified copending application is incorporated herein by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [3] represents the 3rd reference cited in the reference list, namely, Gao X, Cui Y, Levenson R M, Chung L W, Nie S, Nat Biotechnol, 22:969-976, 2004.

STATEMENT AS TO RIGHTS UNDER FEDERALLY-SPONSORED RESEARCH

This invention was made with Government support under Contract Nos. R01CA095643 and U54 CA119338-01 awarded by the National Institutes of Health of the United States, and under Contract No. DAMD17-03-1-0665 awarded by the Department of Defense of the United States, respectively. Accordingly, the United States Government may have certain rights in this invention pursuant to these grants.

This application is being filed as PCT International Patent application in the name of Emory University, a U.S. national corporation, Applicant for all countries except the U.S., and Lily Yang, Hui Mao, Shuming Nie, and Xiaohu Gao, all U.S. residents, Applicants for the designation of the U.S. only, on 4 May 2007.

FIELD OF THE INVENTION

The present invention relates generally to nanostructures, and in particular to multifunctional nanostructures for in vivo tumor imaging and treatment.

BACKGROUND OF THE INVENTION

The application of nanotechnology to cancer research is an exciting frontier in the efforts to develop novel approaches for cancer detection and treatment. Although the feasibility of using nanoparticles for cancer detection and drug delivery has been demonstrated in several laboratories [1-3], a major obstacle limiting its clinical application is that non-tumor targeted nanoparticles are unable to reach sufficient concentration in the tumor site to either produce a strong signal for tumor imaging or to carry optimal amounts of therapeutic agents into tumor cells.

Breast cancer is the most common type of cancer and a leading cause of death among women. Crucial factors that would increase patient survival are early detection and effective treatment. The development of novel approaches for detecting and treating breast cancer are urgently needed to increase patient survival. Furthermore, since cancer metastasis is the main cause for the mortality in breast cancer patients. Any new approaches for detection and targeted treatment of distant metastases should also significantly improve patient prognosis.

Although various imaging technologies and modalities have been widely used for management of cancer including diagnosis and treatment monitoring, conventional tumor imaging methods such as magnetic resonance imaging (MRI), X-ray computerized tomography (CT) or even positron emission tomography (PET) have their limitations in both specificity and sensitivity of cancer detection [4-6]. Increasing evidence suggests that the use of targeted imaging probes enhances signal intensity in the tumor, increasing the sensitivity of the detection [7-10]. Furthermore, imaging agents that target changes in the tumor environment, such as tumor endothelial cells and intra-tumor stromal cells, should further augment tumor imaging signals [11].

It is clear that selective delivery of therapeutic agents into a tumor mass has the potential to minimize toxicity to normal tissues, while improving bioavailability of cytotoxic agents in the tumor [12, 13]. Antibodies, ligands and peptides that target to cell surface molecules, which are highly expressed in tumor cells or tumor endothelial cells have been used to deliver therapeutic agents, showing promise in achieving tumor specific cytotoxicity [3, 14]. An important way to improve the delivery of therapeutic agents is to limit the size of the delivery complex in many currently used delivery systems such as antibody-conjugates, liposomes and other macromolecules, since it is well known that solid tumors will show very poor bio-distribution of the large molecules due to the dysfunctional blood and lymphatic vessels and compressive pressure in the tumor [15-17]. Therefore, the use of drug delivery vehicles with sizes of a few nanometers will enhance the efficiency of delivery of therapeutic agents into solid tumors.

Additionally, tumor imaging plays a key role in helping clinicians to detect solid tumors, to determine tumor recurrence and to evaluate the response of the tumors to therapeutic reagent. The combination of imaging technology and tumor biology has created a "molecular imaging" field with new applications in all imaging modalities. The methods for high-resolution in vivo imaging using mainly three types of imaging probes: radio-labeled, magnetic and optical probes for PET and single photon emission tomography (SPECT); MRI and spectroscopy; and optical imaging techniques, including fluorescence-mediated tomography (FMT) and near-infrared fluorescence (NIRF) reflectance imaging. Although different modalities vary in imaging sensitivity and resolution, the technical challenge in improving target specificity and sensitivity is common. In a clinical practice, for example, $^{18}$F-fluoro-2-deoxy-D-glucose (FDG) and Gd(III)-aminobenzyl-diethylenetriaminepentaacetic acid (Gd-DTPA) contrast agent are used commonly for PET and MRI, respectively. However, both have significant limitations in sensitivity and specificity in delineating tumor and detecting cancer cells in the early stage of development of tumor [5, 44, 45]. Recently, tumor-targeted optical, radio- or magnetic probes have been generated and the feasibility of those imaging probes was examined in both animal tumor models and in clinical studies [1, 7, 10, 46, 47]. Those results show that tumor-targeted imaging probes can increase the localization of the image probes in tumors while reducing their uptake in normal tissues. However, to develop a promising tumor imaging approach to clinical applications, several important issues have to be addressed in the research laboratory. The most important issues include: 1) developing of imaging probes that emit a strong signal to improve sensitivity of detection; 2) targeting probes to cellular receptors that are highly expressed in human tumor cells or tumor environments and demonstrating that there is low toxicity to normal organs and tissues; and 3) developing an effective delivery system to direct the imaging probe to the targeted tumor or cancer cells.

At present, three types of imaging probes are used for in vivo imaging: optical, magnetic and radio labeled probes. Optical image probes use organic fluorescence dyes, fluorescence proteins, and semiconductor quantum dots. Emerging as a new class of fluorescent probes for in vivo biomolecular and cellular imaging, these quantum dots (QDs) are tiny, nanometer-scale light-emitting particles. In comparison with organic dyes and fluorescent proteins, quantum dots have unique optical and electronic properties such as size-tunable light emission, improved signal brightness, resistance against photobleaching, and ability to simultaneous excite multiple fluorescence colors [48]. These properties are most promising for improving the sensitivity of molecular imaging and quantitative cellular analysis by 1-2 orders of magnitude. Nie et al. first reported that it is feasible to simultaneously target and image prostate tumors in living animal models using bioconjugated prostate membrane antigen-targeted QDs [1]. This new class of QD conjugates contains an amphiphilic triblock copolymer layer for in vivo protection and multiple PEG molecules for improved biocompatibility and circulation, making it highly stable and able to produce bright signals. This triblock copolymer layer is designed so that it can have multiple active functional groups for conjugation of different tumor targeting moieties and therapeutic agents on the same nanoparticle. Another advantage is that multicolor QD probes can be used to image and track multiple tumor markers simultaneous, which will most likely increase the specificity and sensitivity of cancer detection.

Recently, QDs producing near infrared (NIR) signals have also been developed [49, 50]. NIR light penetrates much more deeply into tissues, compared to visible fluorescence, and allows detection of signals inside animals. The feasibility of detection of NIR signals in animal tumor models has been demonstrated using fluorescent dye Cy 5.5-labeled RGD peptide or an enzyme-activated Cy 5.5 NIR signal [10, 51, 52]. Detection of QD NIR signals in sentinel lymph node in large animals real time has also been demonstrated [50, 53]. A major advantage of NIR QDs is that emissions of those QDs are well beyond the spectral range of autofluorescence in tissues, thus resulting in imaging with a high signal:background ratio [53].

In comparison to optical imaging, magnetic resonance imaging (MRI) has lower sensitivity when applied for molecular and cellular imaging. However, it has super imaging resolution and deep tissue penetration for visualizing abnormalities in small animal and human using tissue water molecules as signal sources. It is a non-invasive imaging modality and is routinely used in the clinic for diagnostic imaging. To obtain contrast enhancement and signal amplification, paramagnetic contrast agents are often used. Although Gd-DTPA, a blood-pool contrast agent, is widely accepted in the clinical uses, superparamagentic iron oxide (SPIO or IO) nanoparticles are emerging as a new generation of MRI contrast agent for the development of target specific contrast agent, because it has a long blood retention time, low toxicity and biodegradability. The IO nanoparticles possess unique paramagnetic properties, which generate significant susceptibility changes resulting in strong $T_2$ and $T^*_2$ contrast [45, 54]. In addition, the surface coating molecules used for the IO nanoparticles can be conjugated to the biomolecule to provide target specific interaction to the cell [54]. Several recent studies have demonstrated that the IO nanoparticles can be internalized by various cell lines including cancer cells to allow magnetically labeling of the targeted cell. When internalized by cells, the IO nanoparticles are able to generate MRI contrast that enables single-cell MR detection [55]. At present, non-targeted IO particles has been used in clinic and is proven to be safe for human use.

Over the past years, significant efforts have gone toward developing a target specific MRI contrast agent based on the formulation of the IO nanoparticles [56-59]. However, several obstacles remain to be overcome. The major challenge is to develop a surface coating material that not only can stabilize the nanoparticles but also to provide active functional groups available for controllable bioconjugation of "probe" ligands. Traditional ligands (e.g., dextran) that are used for the stabilization of magnetic nanocrystals often have weak ligand-particle interactions, so they can be easily detached from the nanocrystal surface, leading to nanoparticle aggregation and eventually precipitation even under physiological conditions or even just during storage. Since further derivatization is needed, such a weak interaction between ligand and particle may not withstand the required reaction conditions.

Therefore, a heretofore-unaddressed need exists in the art to address the aforementioned deficiencies and inadequacies.

SUMMARY OF THE INVENTION

The present invention, in one aspect, relates to a nanostructure. In one embodiment, the nanostructure has a magnetic iron oxide nanoparticle; a hydrophobic protection structure including at least an amphiphilic copolymer, where the hydrophobic protection structure at least partially encapsulates the magnetic iron oxide nanoparticle; and at least one amino-terminal fragment (ATF) peptide or single chain anti-epidermal growth factor receptor (EGFR) antibody conjugated to the amphiphilic copolymer protection structure.

The nanostructure further includes a probe disposed on the amphiphilic polymer protection structure, where the probe comprises an antibody, a polypeptide, a polynucleotide, a drug molecule, an inhibitor compound, or any combination thereof.

The magnetic iron oxide nanoparticle, in one embodiment, has a core size of about 1-50 nm. The magnetic iron oxide nanoparticle can be a superparamagnetic iron oxide nanoparticle.

In one embodiment, the least one ATF peptide is corresponding the amino-terminal fragments (from 1 to 40, 20 to 30, or 1 to 135 amino acids) of a urokinase plasminogen activator (uPA). The least one EGFR antibody is corresponding to a single chain antibody to the epidermal growth factor receptor (ScFvEGFR). Accordingly, the nanostructure is capable of targeting to urokinase plasminogen activator receptor (uPAR)-expressing tumor cells or EGFR-expressing tumor cells. In one embodiment, the at least one ATF peptide or EGFR antibody is labeled with a fluorescence dye, where the fluorescence dye is a Cy5.5, or other dyes such as ICG.

The amphiphilic copolymer includes an amphiphilic block copolymer, an amphiphilic random copolymer, an amphiphilic alternating copolymer, an amphiphilic periodic copolymer, or any combination thereof. The amphiphilic block copolymer comprises a diblock copolymer, a triblock copolymer, or any combination thereof. In one embodiment, the amphiphilic block copolymer includes an ABC triblock structure having one or more grafted 8-carbon alkyl side chains, where the ABC triblock structure includes a poly-butylacrylate segment, a poly-ethylacrylate segment, and a poly-methacrylic acid segment. In one embodiment, the amphiphilic copolymer has a molecular weight of about 10,000 to 200,000.

In another aspect, the present invention relates to a pharmaceutical composition comprising the nanostructure as disclosed above. The pharmaceutical composition further comprises a probe releasably attached onto the nanostructure, where the probe comprises an antibody, a polypeptide, a polynucleotide, a drug molecule, an inhibitor compound, or any combination thereof.

In yet another aspect, the present invention relates to a method of synthesizing a nanostructure. The nanostructure as formed is stable, water soluble and biocompatible. In one embodiment, the method includes the steps of providing a magnetic iron oxide nanoparticle; forming a hydrophobic protection structure around the a magnetic iron oxide nanoparticle, where the hydrophobic protection structure includes at least an amphiphilic copolymer; and conjugating at least one amino-terminal fragment (ATF) peptide or epidermal growth factor receptor (EGFR) antibody to the hydrophobic protection structure.

The method further includes the step of labeling the at least one ATF peptide or EGFR antibody with a fluorescence dye, where the fluorescence dye is a Cy5.5.

The method may also includes the step of disposing a probe on the hydrophobic protection structure, where the probe comprises an antibody, a polypeptide, a polynucleotide, a drug molecule, an inhibitor compound, or any combination thereof.

In one embodiment, the providing step includes the steps of forming a mixture having iron oxide powders, an oleic acid and an octadecene (ODE); and heating the mixture at a temperature greater than about 300° C. for a period of time effective to form magnetic iron oxide nanoparticles. As formed, the magnetic iron oxide nanoparticle has a core size that is tunable by changing at least one of a plurality of factor consisting of the heating temperature, the period of time, and concentrations of the iron oxide and the oleic acid in the mixture, respectively. The core size of the magnetic iron oxide nanoparticle, in one embodiment, is about 1-50 nm.

In one embodiment, the amphiphilic copolymer comprises an amphiphilic block copolymer, an amphiphilic random copolymer, an amphiphilic alternating copolymer, an amphiphilic periodic copolymer, or any combination thereof.

In a further aspect, the present invention relates to a nanostructure. In one embodiment, the nanostructure has a nanospecies; and at least one amino-terminal fragment (ATF) peptide or epidermal growth factor receptor (EGFR) antibody conjugated to the nanospecies, where the at least one ATF peptide or EGFR antibody is labeled with a fluorescence dye.

The nanostructure further has a hydrophobic protection structure formed between the nanospecies and the at least one ATF peptide or EGFR antibody, where the hydrophobic protection structure includes at least an amphiphilic copolymer.

The nanostructure may also include a probe deposed on the hydrophobic protection structure, where the probe comprises an antibody, a polypeptide, a polynucleotide, a drug molecule, an inhibitor compound, or any combination thereof.

The nanospecies is visible in magnetic resonance imaging (MRI). In one embodiment, the nanospecies includes a magnetic iron oxide nanoparticle, where the magnetic iron oxide nanoparticle has a core size of about 1-50 nm.

In yet a further aspect, the present invention relates to a pharmaceutical composition. In one embodiment the pharmaceutical composition includes the nanostructure as disclosed above. The pharmaceutical composition also includes a probe releasably attached onto the nanostructure, where the probe comprises an antibody, a polypeptide, a polynucleotide, a drug molecule, an inhibitor compound, or any combination thereof.

In one aspect, the present invention relates to a tumor-targeted multifunctional nanoprobe. In one embodiment, tumor-targeted multifunctional nanoprobe has a nanospecies; a hydrophobic protection structure encapsulating the nanospecies; at least one amino-terminal fragment (ATF) peptide or epidermal growth factor receptor (EGFR) antibody conjugated to the amphiphilic structure; a fluorescence dye labeled to the at least one ATF peptide or EGFR antibody; and a probe deposed on the hydrophobic protection structure, where the probe comprises an antibody, a polypeptide, a polynucleotide, a drug molecule, an inhibitor compound, or any combination thereof.

The nanospecies is visible in magnetic resonance imaging (MRI). In one embodiment, the nanospecies includes a magnetic iron oxide nanoparticle, where the magnetic iron oxide nanoparticle has a core size of about 1-50 nm.

In one embodiment, the hydrophobic protection structure includes at least an amphiphilic copolymer, where the amphiphilic copolymer comprises an amphiphilic block copolymer, an amphiphilic random copolymer, an amphiphilic alternating copolymer, an amphiphilic periodic copolymer, or any combination thereof.

In another aspect, the present invention relates to a method for target imaging and/or therapy. In one embodiment, the method includes the step of providing a nanostructure having a nanospecies; a protection structure including at least an amphiphilic copolymer, where the amphiphilic protection structure at least partially encapsulates the nanospecies; and at least one amino-terminal fragment (ATF) peptide or epidermal growth factor receptor (EGFR) antibody conjugated to the amphiphilic protection structure. Furthermore, the method includes the steps of introducing the nanostructure into a subject; and determining the presence of the target in the subject by detecting the nanostructure. In one embodiment, the target is a cancerous disease, where the cancerous disease is a tumor. The tumor, in one embodiment, is at least one of pancreatic cancer and breast cancer.

The nanospecies is visible in magnetic resonance imaging (MRI), where the nanospecies comprises a magnetic iron oxide nanoparticle. The at least one ATF peptide or EGFR antibody is labeled with a fluorescence dye.

In one embodiment, the nanostructure further has a probe deposed on the amphiphilic protection structure, where the probe comprises an antibody, a polypeptide, a polynucleotide, a drug molecule, an inhibitor compound, or any combination thereof.

In one embodiment, the introducing step is performed by a subcutaneous injection or a systemic injection. When the introducing step is performed by a systemic injection, a plurality of the nanostructure is accumulated substantially in the target region of the subject.

The determining step is performed in vivo. In one embodiment, the determining step includes the step of acquiring an image of the target. The determining step may include a passive targeting process or an active targeting process.

In yet another aspect, the present invention relates to a method for target imaging and/or therapy. The method in one embodiment includes the step of providing a nanostructure having a nanospecies visible in at least one imaging modality and at least one amino-terminal fragment (ATF) peptide or epidermal growth factor receptor (EGFR) antibody conjugated to the nanospecies. The at least one ATF peptide or EGFR antibody is labeled with a fluorescence dye. The at least one imaging modality is corresponding to magnetic resonance imaging (MRI) and optical imaging.

In one embodiment, the nanospecies has a magnetic iron oxide nanoparticle. The nanostructure further comprises a probe attached to the nanospecies, where the probe comprises an antibody, a polypeptide, a polynucleotide, a drug molecule, an inhibitor compound, or any combination thereof.

The method also includes the step of introducing the nanostructure into a subject, thereby causing selective accumulation of the nanostructure in a target region of the subject, where the target is a cancerous disease. The subject can be a living subject such as an animal or a human being. In one embodiment, the introducing step is performed by a subcutaneous injection or a systemic injection.

The method further includes the steps of acquiring at least one image of the target; and determining the presence of the target in the subject from the acquired at least one image of the target. The at least one image of the target includes at least one of an MRI image and a florescence image.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE PREFERRED EMBODIMENTS

Figure 1:
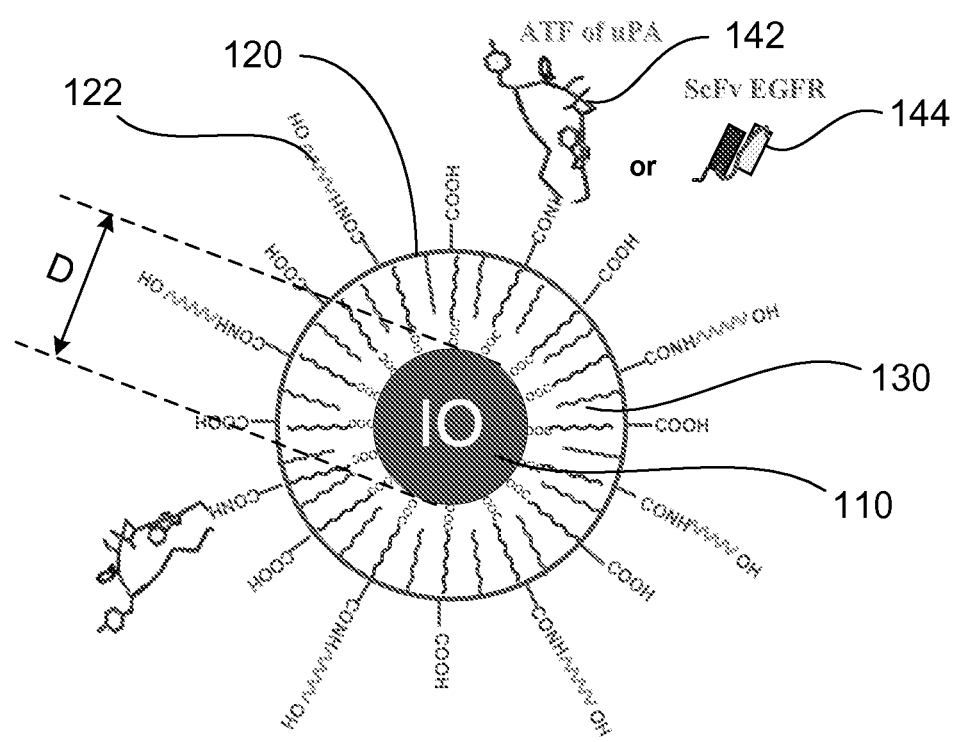
FIG. 1 shows schematically targeted IO nanoparticles according to one embodiment of the present invention, where an amphiphilic polymer coated IO-nanoparticle is conjugated with an amino-terminal fragment (ATF) peptide of a urokinase plasminogen activator (uPA) or a single chain antibody to the epidermal growth factor receptor (ScFvEGFR).

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "quantum dot" as used herein refers to a quantum-confined particle or a semiconductor crystal that confines electrons, holes, or electron-hole pairs or so-called excitons to a region on the order of just a few nanometers. The quantum dot (QD) exhibits unique optical and electronic properties, such as size- and composition-tunable fluorescence emission from visible to infrared wavelengths, large absorption coefficients across a wide spectral range, and very high levels of brightness and photostability.

The term "copolymer" as used herein refers to a polymer formed when two (or more) different types of monomer are linked in the same polymer chain. The assembly of the monomers in the copolymers can be head-to-tail, head-to-head, or tail-to-tail. Since a copolymer consists of at least two types of repeating units (not structural units), copolymers can be classified, based on how these units are arranged along the chain, as random copolymer, alternating copolymer, block copolymer, graft copolymer, star copolymers, and brush copolymers.

The block copolymers are made up of blocks of different polymerized monomers. For example, polystyrene-b-poly(methyl methacrylate) (PS-b-PMMA) is made by first polymerizing styrene, and then subsequently polymerizing MMA. This polymer is a diblock copolymer because it contains two different chemical blocks. One can also make triblocks, tetrablocks, pentablocks, etc.

The term "dendrimer" as used herein refers to a molecule with a form like the branches of a tree. The properties of dendrimers are dominated by the functional groups on the molecular surface. For example, a dendrimer can be water-soluble when its end-group is a hydrophilic group, like a carboxyl group. For a water-soluble dendrimer with internal hydrophobicity, it can be used to carry a hydrophobic drug in its interior. Another property of dendrimers is that the volume of a dendrimer increases when it has a positive charge. If this property can be applied, dendrimers can be used for drug delivery systems (DDS) that can give medication to the affected part inside a patient's body directly.

Acronyms and abbreviations used herein, "ATF" refers to an amino-terminal fragment; "uPA" refers to a urokinase plasminogen activator; "EGFR" stands for an epidermal growth factor receptor; "ScFvEGFR" represents a single chain antibody to the EGFR; "QD" stands for a quantum dot; "IO" represents an iron oxide; "ATF-IO" refers to ATF conjugated IO; and "ScFvEGFR-IO" refers to a ScFvEGFR conjugated iron oxide.

Overview of the Invention

Development of human cancer is a multistage process involving various genetic alternations and cellular abnormalities that provide advantages for the growth and progression of tumors [18]. The differences in the expression of cellular receptors between normal and tumor cells provide a great opportunity for targeting nanoparticles to the altered cancer cell surface molecules.

Urokinase plasminogen activator (uPA) is a serine protease that regulates multiple pathways involved in matrix degradation, cell motility, metastasis and angiogenesis [6, 19]. Interaction of the N-terminal growth factor domain of uPA with its cellular receptor (uPAR) results in the conversion of the plasminogen to a serine protease, which is a central regulator of the activation of other proteases including the matrix metalloproteinases (MMPs) [19]. Studies have shown that the uPA/uPAR complex controls the motility of both tumor and endothelial cells [20]. In addition to its role in activation of the process for degradation of extracellular matrix, uPAR also activates $\alpha 5 \beta 1$ integrin and ERK signaling through interaction with a human epidermal growth factor receptor (EGFR) and induces cell proliferation [21]. Additionally, the uPA/uPAR complex can bind to the matrix protein, vitronectin, in association with transmembrane integrins, and activate intracellular signaling molecules such as the protein kinases, promoting cell adhesion, proliferation, and migration [22].

The cellular receptors for uPA (uPAR) are highly expressed in many human tumor cells, intratumoral fibroblasts and tumor endothelial cells. About 54% of ductal carcinoma in situ (DCIS) and 73% of lobular carcinoma tissues have over 50% of their cancer cells overexpressing uPAR [23]. An elevated level of uPAR is associated with tumor aggressiveness, the presence of distant metastasis and poor prognosis [24]. However, uPAR is undetectable in the majority of normal tissues or organs except for low levels expressed in macrophages, granulocytes, the uterus, thymus, kidney and spleen [25]. Therefore, uPAR is an excellent molecular target for recruiting nanoparticles to breast tumor sites.

The uPAR-binding domain of uPA is located to the amino-terminal fragment (ATF) of uPA [26]. Studies have shown that ATF is a potent uPA binding antagonist to its high affinity receptor (uPAR) at the surface of both tumor and endothelial cells [27, 28]. Systemic or local delivery of a non-catalytic ATF of uPA (residues 1-135) using an adenoviral vector or conjugated peptides prevents the formation of the uPA/uPAR complex, thus inhibiting tumor growth and angiogenesis [27]. Therefore, ATF peptide should represent a very good candidate for engineering multifunctional nanoparticles to target breast cancer.

The EGFR family includes EGFR (HER-1), EGFR-2 (HER-2), EGFR-3 (Her-3) and EGFR 4 (HER-4). The ligands that bind to EGFRs are divided into EGFR-like ligands such as EGF and TGF-$\alpha$, and the heregulins. These ligands bind to EGFR monomers to promoter receptor dimerization and oligomerization, that ultimately results in the activation of the EGFR signaling pathway [29]. This EGFR signaling pathway plays a key role in the regulation of cell proliferation, survival and differentiation. As EGFR is one of the best studied ligand-receptor system and specific approaches for inhibition of EGFR signaling are currently among the most advanced and promising therapies currently undergoing preclinical and clinical studies [30-32].

It has been shown that 14 to 91% of human breast carcinomas express high levels of the EGF receptors [33, 34]. About $10^6$ of EGFR are detected in a single breast cancer cell in vitro [35]. Overexpression of this receptor has been associated with highly aggressive breast cancer types and a poor response to therapeutic agents [34, 36, 37]. Prior preclinical and clinical studies have shown that blocking the EGFR via monoclonal antibodies or inhibition of EGFR tyrosine kinase with small molecule inhibitors inhibits the growth of breast cancers and sensitize chemotherapy responses [38, 39]. Although the efficacy of EGFR blocking monoclonal antibody has been demonstrated in clinical trials [40], the size of this antibody is very large (150-170 KDa) and is not ideal for efficient conjugation to nanoparticles. The large size of the intact antibody also limits the ability of the nanoparticle probes to diffuse from the vasculature into areas with tumor cells. In addition, the interaction of antibody with Fc receptors on normal tissues with an antibody can alter the specificity of tumor-targeted nanoparticles. To solve those problems, single-chain antibodies to EGFR that contain the specific EGFR binding region but lack the Fc region have been isolated from human ScFv phage display libraries [41], and their inhibitory effects on tumor cell proliferation have already been shown in several laboratories [42, 43].

Magnetic iron oxide (IO) nanoparticles and their derivatives have been tested as magnetic resonance imaging (MRI) contrast agents and can be used in human. Their long blood retention time, low toxicity and biodegradability are attractive properties for developing target specific imaging [11, 12]. IO nanoparticles possess unique paramagnetic properties resulting change of relaxivities of water for MRI contrast. Recent studies have demonstrated that IO nanoparticles can be internalized by cells, generating significant susceptibility changes resulting in strong $T_2$ and $T_2$ contrast for MR detection of magnetically labeled cells [13]. By modifying its coating material and surface chemistry, selected molecules can be conjugated to IO, providing functionalities and specificity.

The present invention, among other things, explores and utilizes IO nanoparticles, uPA, uPAR, and EGFR with other inventive aspects as set forth below, to detect and/or treat tumor, cancer and/or other diseases.

The present invention in one aspect relates to one or more multifunctional nanostructures that selectively target to human tumors for in vivo tumor imaging as well as inhibition of tumor growth holds a great promise for improving survival rate of cancer patients with other inventive aspects as set forth below, to detect and/or treat tumor, cancer and/or other diseases. In another aspect, the present invention relates to methods of engineering such nanostructures with uniformly sized IO nanoparticles with functionalized surface to conjugate targeted peptides and single chain antibodies. The IO nanoparticles include, but are not limited to, superparamagnetic iron oxide nanoparticles. Using these approaches, IO nanoparticles targeting uPAR and EGFR are obtained. The engineered IO nanostructures exhibit the specificity in breast and pancreatic cancer cells in vitro and in vivo and target specific contrast in MR imaging of a pancreatic xenograft cancer model in nude mice. This tumor targeted nanostructures (MRI probe) have the potential for detection of primary and metastatic pancreatic cancer and breast cancer.

In one embodiment, the present invention discloses nanostructures having peptide conjugated IO nanoparticles targeting to uPAR or a single chain antibody to epidermal growth factor receptor (ScFvEGFR), which are highly expressed in human breast cancer and pancreatic cancer tissues. It is demonstrated that the IO nanoparticles bind to and are internalized by pancreatic cancer cells in vitro, resulting a significant shortened T2 detected by MRI scans and positive Prussian blue staining in the tumor cells. Furthermore, the targeted-IO nanoparticles markedly inhibit the growth of pancreatic cancer cells in vitro. Using an orthotopic human pancreatic cancer xenograft model in nude mice, in vivo MRI demonstrates that the systemic delivery of the targeted IO nanoparticles leads to accumulation of the IO nanoparticles in intra-pancreatic tumors causing a significant signal drop in those areas. Examination of tissue distribution of the target-IO nanoparticles by Prussian blue staining of frozen tissue sections shows high levels of iron staining in pancreatic cancer lesions but not in adjacent normal pancreas. Normal liver and spleen also display high levels of iron staining, while normal lung tissue has a low level of iron staining. Both kidney and heart tissues are lack of iron staining. Therefore, the multifunctional nanoparticles have potential for the development of tumor-targeted imaging probes and drug delivery particles for the detection and treatment of breast and pancreatic cancers.

Referring to FIG. 1, a nanostructure 100 is shown according to one embodiment of the present invention. The nanostructure 100 has an IO nanoparticle 110, a hydrophobic protection structure 130 encapsulating the IO nanoparticle 110, and one or more ATF peptides 142 or EGFR antibodies 144 conjugated to the amphiphilic copolymer 130. The one or more ATF peptides 142 are corresponding to ATFs of uPA. The one or more EGFR antibodies 144 are corresponding to ScFvEGFRs. Accordingly, the nanostructure 100 is capable of targeting to uPAR-expressing tumor cells or EGFR-expressing tumor cells, for example, in a breast cancer and a pancreatic cancer.

The IO nanoparticle 110 can be formed by heating a mixture having iron oxide powders, an oleic acid and an octadecene (ODE), at a temperature greater than about 300° C. for a period of time. The core size, D, of the IO nanoparticles is tunable by changing the heating temperature, the period of time, and concentrations of the iron oxide and the oleic acid in the mixture. In one embodiment, the core size D of the IO nanoparticle 110 is about 1-50 nm. The IO nanoparticle 110 is visible in the MRI imaging.

The hydrophobic protection structure 130 includes at least an amphiphilic copolymer 120 grafted with carbon alkyl side chains 122 to which the one or more ATF peptides 142 or EGFR antibodies 144 are conjugated.

The amphiphilic copolymer includes an amphiphilic block copolymer, an amphiphilic random copolymer, an amphiphilic alternating copolymer, an amphiphilic periodic copolymer, or any combination thereof, where the amphiphilic block copolymer comprises a diblock copolymer, a triblock copolymer, or any combination thereof. The amphiphilic block copolymer includes an ABC triblock structure having grafted 8-carbon alkyl side chains, where the ABC triblock structure includes a poly-butylacrylate segment, a poly-ethylacrylate segment, and a poly-methacrylic acid segment. The amphiphilic copolymer has a molecular weight of about 10,000 to 200,000.

Additionally, the one or more ATF peptide or EGFR antibody may be labeled with a fluorescence dye, for example, Cy5.5. This makes the nanostructure 100 visible in the near infrared fluorescence imaging. Other dyes such as ICG can also be used to practice the present invention.

The nanostructure 100 may further include a probe or drug agent (not shown) attached onto the amphiphilic copolymer layer. The probe or drug agent may comprise an antibody, a polypeptide, a polynucleotide, a drug molecule, an inhibitor compound, or any combination thereof. Once the nanostructure 100 targets to, and specifically binds to and is internalized by uPAR- or EGFR-expressing tumor cells, the probe or drug agent may be released to its surrounding environment, thereby causing inhibiting of the growth of the uPAR- or EGFR-expressing tumor cells, and/or killing of the uPAR- or EGFR-expressing tumor cells.

Therefore, the nanostructure according to one embodiment of the present invention can be utilized as a tumor-targeted multifunctional nanoprobe, which not only detects the presence of tumor cells of a cancer by acquiring an MRI image and/or fluorescence image from a target of interest, but also treats the tumor cells by releasing a drug agent attached to the nanostructure therein. The target of interest may be a cancerous disease including a tumor. The tumor is at least one of pancreatic cancer and breast cancer.

The present invention, in one aspect, relates to a pharmaceutical composition comprising the nanostructure as disclosed above. A probe including an antibody, a polypeptide, a polynucleotide, a drug molecule, an inhibitor compound, or the like, is releasably attached onto the nanostructure. The pharmaceutical composition is usable for treatment of a cancer disease. Such treatment can be monitored in real-time by acquiring MRI image and/or fluorescence image of the target.

In a further aspect, the present invention relates to a method of synthesizing a nanostructure. The method includes the steps of providing an IO nanoparticle, forming a hydrophobic protection structure around the IO nanoparticle, wherein the hydrophobic protection structure includes at least an amphiphilic copolymer, and conjugating at least one ATF peptide or EGFR antibody to the hydrophobic protection structure.

It would be obvious for people skilled in the art that other types of nanospecies can also be utilized to practice the present invention, as long as the nanospecies is visible in an MRI and optical imaging.

These and other aspects of the present invention are more specifically described below.

EXAMPLES

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Receptor-Targeted Nanoparticle for In Vivo Targeting and Non Invasive Imaging of Cancer Experimental Methods Breast Cancer Cell Lines:

Mouse mammary carcinoma cell line 4T1B was provided by the Barbara Ann Karmanos Cancer Institute, Detroit, Mich. 4T1 cell line stable expressing a firefly luciferase gene was obtained by Duke University, Durham, N.C. Human breast cancer cell line T47D was purchased from American Type Culture Collection (ATCC, Rockville, Md.). 4T1 cells were grown in Dulbecco's modified Eagle's medium containing 10% fetal bovine serum (FBS). T47D cells were grown in RPMI 1640 containing 10% FBS, 100 ug/ml gentamicin, and 0.2 IU insulin/ml.

Engineering ATF-IO Nanoparticles:

A cDNA fragment encoding amino acids 1-135 of mouse uPA, isolated by PCR amplification using a PCR primer pair containing forward (5'-CACCATGGGCAGTGTACTTG-GAGCTCC-3') and reverse (5'-GCTAAGAGAGCAGTCA-3') primers, was cloned into pET101/D-TOPO expression vector (Invitrogen, Carlsbad, Calif.). The cDNA sequences were confirmed by DNA sequencing. Recombinant ATF peptides were expressed in *E. coli* BL21 (Invitrogen) and purified from bacterial extracts under native conditions using a Ni2+ NTA-agarose column (Qiagen, Valencia, Calif.). Purification efficiency was determined using electrophesis on sodium dodecyl sulfate (SDS)-PAGE gel and greater than 95% of purified proteins were ATF peptides.

A near infrared dye, Cy5.5™ maleimide (GE Healthcare UK Ltd, England), was conjugated to ATF peptides using the manufacture's protocol. Unconjugated dye molecules were separated from the Cy5.5 labeled ATF peptides using Sephadex G25 column.

Figure 2:
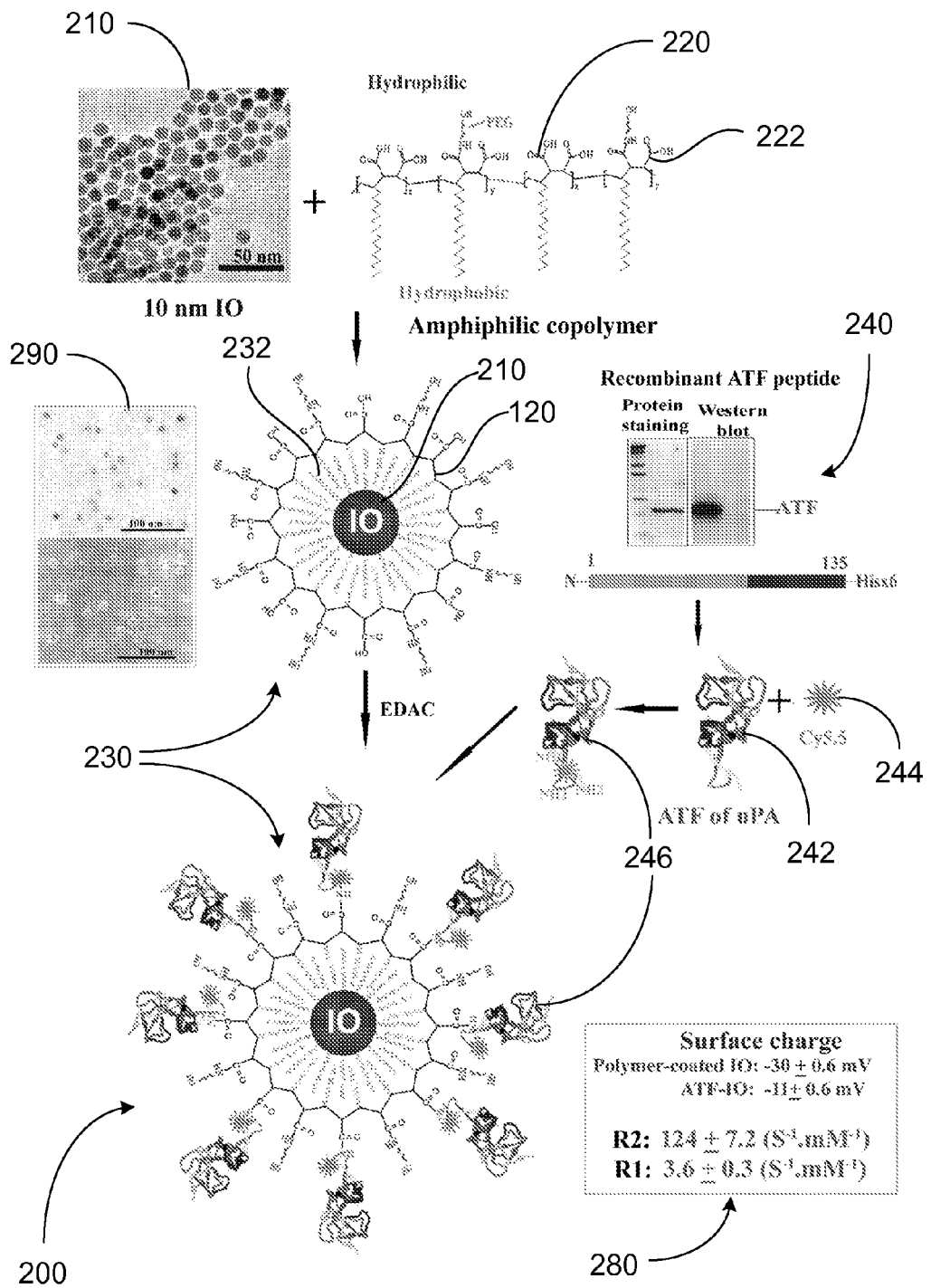
FIG. 2 shows schematically production of ATF-IO nanoparticles according to one embodiment of the present invention. Uniform size of about 10 nm IO nanoparticles demonstrated by transmission electron microscopy (TEM) were coated with amphiphilic copolymers modified with short PEG chains. The purity of recombinant ATF peptides produced from a bacterial expressing system was confirmed by Crossman blue staining on SDS-PAGE gel as well as Western blots using an anti-His tag antibody. Cy5.5™ maleimide was conjugated to the ATF peptides through a disulfide bond. The ATF peptides or Cy5.5-ATF-IO peptides were then conjugated to the carboxyl side groups mediated by EDAC. About 8 to 10 ATF peptides were conjugated to the surface of an 10 nanoparticle. Changes in surface charge of ATF-peptide conjugated or unconjugated 10 nanoparticles were determined by Zeta potential measurement. A reduction in the value of negative charge indicates replacing carboxyl side group with ATF peptides. MRI of the ATF-IO nanoparticles in solution reveals a strong $T_2$ relaxivity of 124 $S^{-1} \cdot mM^{-1}$ (R2) and a low T1 relaxivity (R1).

Paramagnetic iron oxide nanoparticles with a uniform size were prepared using iron oxide powder as the iron precursor, oleic acid as the ligands, and octadecene (ODE) as the solvent. For a typical synthesis, iron oxide powder is dissolved by oleic acid upon heating to about 200° C., resulting in an iron oleate complex. This complex became unstable when temperature reached higher than 250° C. The black magnetite nanocrystals can be formed at about 300° C. After the reaction is completed, the reaction mixture is cooled down and the nanocrystals are collected as precipitate by adding chloroform and acetone into the reaction mixture. The size of IO nanoparticles was controlled by changes in heating time, temperature, and concentration of the iron oxide and oleic acid. The core size and hydrodynamic size of the IO nanoparticles were determined using transmission electron microscopy (TEM), and light scattering scan or zeta potential measurement, respectively. In one embodiment, the IO nanoparticles with a core size of about 10 nm are chosen according to the exemplary embodiment of practice the present invention. To stabilize and functionalize the surface of the IO nanoparticles, the particles were coated with amphiphilic polymers using a similar method developed by Gao et al. [3], which provides carboxylate groups with negatively charged surface. Each nanoparticle has about 200 carboxyl side groups, of which a half of the carboxyl groups were further conjugated to short PEG chains and remaining free carboxyl groups for peptide conjugation. ATF peptides were conjugated to the surface of the IO nanoparticles via cross-linking of carboxyl groups to amino side groups on the ATF peptides. The procedure of engineering an ATF-IO or Cy5.5-ATF-IO is shown in FIG. 2. Briefly, the polymer-coated IO nanoparticles were activated with about 2 mM ethyl-3-dimethyl amino propyl carbodiimide (EDAC, Pierce, Rockford, Ill.) and about 5 mM N-Hydroxysulfosuccinimide (Sulfo-NHS, Pierce) for about 15 min at room temperature. After purification, activated IO nanoparticles were reacted with ATF or Cy5.5-ATF peptides at an IO:ATF molar ratio of about 1:20 at pH 7 for overnight at about 4° C., generating ATF-IO or Cy5.5-ATF-IO nanoparticles. The final ATF-IO conjugates were purified using 100 k filter column filtration and centrifuged at about 9600 rpm for about 20 min. After washing 3 times with PBS, ATF-IO nanoparticles were resuspended in PBS (pH 7). Conjugation efficiency of ATF peptides to the IO nanoparticles was determined using Cy5.5-ATF-IO particles by fluorescence spectroscopy and by the measurement of changes of $\zeta$ potential of the ATF-IO nanoparticles compared to unconjugated IO nanoparticles. The numbers of ATF peptides conjugated to each IO nanoparticle were determined by measuring the fluorescence intensity of a diluted sample of Cy5.5-ATF-IO at an emission wavelength of about 689 nm and then compared the values to a linear standard curve prepared using various concentrations of Cy5.5-ATF peptides.

Western Blot Analysis:

Western Blot analysis was performed with a standard protocol in the Emory laboratory. To confirm the presence of ATF peptides in SDS/PAGE gel, the protein was transferred to PVDF membranes (Bio-Rad). An anti-His tag monoclonal antibody (Novagen, Madison, Wis.) was used to identify the His-tagged ATF-peptides. After reacting with a HRP-labeled rat anti-mouse IgG antibody, ATF peptide band was detected by Enhanced Chemiluminescence using ECL plus (Amersham International, Buckingham, UK) followed by autoradiography. To determine the level of uPAR, an anti-uPAR polyclonal rabbit antibody (Santa Cruz Biotechnology, Santa Cruz, Calif.) that reacts with both mouse and human uPAR, was used and followed by a HRP conjugated goat anti-rabbit IgG. The protein bands were detected using Enhanced Chemiluminescence.

Ni-NTA-Agarose Pull-Down Assays:

To determine if the purified recombinant ATF peptides, either free peptides or after conjugated to the IO nanoparticles, were still able to bind to uPAR, a combined pull-down and Western blot analyses was performed. Ni2+-NTA-agarose beads were incubated with appropriate concentrations of His-tagged ATF peptides or ATF-IO nanoparticles at about 4° C. for about 30 min. The conjugated beads were then washed twice with binding buffer and incubated with about 500 μg of total cell lysates obtained from 4T1 or T47D cells for about 2 hrs. The bound proteins were eluted from the beads using elution buffer containing about 400 mM imidazole and examined by Western Blot analysis to determine the amount of uPAR pulled down by ATF- or ATF-IO conjugated Ni-NTA agarose beads in each sample as described above.

Immunofluorescence Labeling:

Frozen breast normal and cancer tissue sections were fixed with ice-cold acetone for about 15 min and blocked with about 1% (wt/vol) BSA for about 20 min. The slides were incubated with 5 μg/ml of an anti-uPAR polyclonal rabbit antibody for about 60 min and followed by biotinylated-goat anti-rabbit IgG for 30 min. The slides were then incubated with Texas-red avidin for about 30 min. After washing, the slides were examined under a fluorescence microscope and images were taken using an imaging system (Zeiss Axioplan with Axiovision software, Carl Zeiss MicroImaging, Inc, Thornwood, N.Y.). To detect expression level of uPAR in living cancer cells, cultured cells were dissociated from culture dish and cell suspensions were then incubated with anti-uPAR antibody at about 4° C. for about 30 min. After incubation with FITC-goat anti-rabbit IgG for about 30 min, the cells were placed on glass slides and examined under the fluorescence microscope.

Examination of Specific Binding and Internalization of ATF-IO in uPAR Expressing Cancer Cells:

Cells cultured on glass chamber slides (Nalge Nunc International, Naperville, Ill.) were incubated with Cy 5.5-ATF-IO and unconjugated IO nanoparticles for about 3 hrs at about 37° C. After washed with PBS and fixed with ice-cold acetone, the slides were examined under a confocal microscope (Perkin Elmer Ultraview ERS, PerkinElmer Life And Analytical Sciences, Inc, Wellesley, Mass.). To localize the IO nanoparticles, the cells incubated with Cy5.5 ATF-IO or IO nanoparticles were fixed with about 4% formaldehyde in PBS and Prussian blue staining was used to confirm the presence of iron oxide nanoparticles inside the cells.

Determination of Magnetic Signal after Specific Binding and Internalization of ATF-IO Nanoparticles by MRI Scanning:

about $1\times10^7$ of mouse mammary tumor 4T1 cells or control human breast cancer T47D were harvested from cell culture and incubated in serum free medium containing about 20 μl of unconjugated IO or ATF-IO nanoparticles (about 13.5 nM/ml) at about 37° C. for about 3 hrs. Cells were washed with PBS for 5 times and then embedded in about 0.8% agarose homogeneously in multi-well plates. The plates were then scanned in a 3T MRI scanner using $T_1$-weighted gradient echo and multi-echo $T_2$ weighted fast spin echo imaging sequences to collect a series of TE dependent data points simultaneously (from 30 echo times, TE from about 8-200 ms, with increment of about 8 or 10 ms). $T_2$ values of each sample/well were calculated from obtained MR images by fitting the decay curve on a pixel-by-pixel basis using the non-linear mono-exponential algorithm of $M_i = M_0 * \exp(-TE_i/T2)$.

Mouse Mammary Tumor Models:

(1) Subcutaneous tumor model: Mouse mammary tumor 4T1 cells were injected subcutaneously into the back flank area of 6- to 8-week old female Balb/c or nude mice. The nude mice were used for optical imaging to reduce background fluorescence. (2) Intraperitoneal metastatic mammary tumor model: 4T1 cells stably transfected with a firefly luciferase gene were directly injected into up-right side of the peritoneal cavity. The growth of intraperitoneal tumors was monitored by bioluminescence imaging using Xenogen bioluminescence imaging system.

In Vivo MR Imaging of Mouse Mammary Tumors.

Upon the tumors grew to appropriate sizes or detectable by bioluminescence imaging, tumor bearing mice were examined using a 3T MRI scanner to obtain pre-IO contrast MR images. The imaging sequences included: T1 and T2 weighted spin echo or gradient echo methods with a customized rodent coil. The three-dimensional-fast spoiled gradient echo technique (TR/TE=31.2 msec/8 msec; TI=71 msec; flip angle=30° with 512 frequency encoding steps and 256 phase encoding steps, and 40 slices at 0.5 mm slice thickness without gap). A multi-echo T2 weighted fast spin echo sequence was used to obtain T2 relaxometry of the whole mouse. The mice were injected with about 0.2 or 0.28 nmole of ATF-IO or IO nanoparticles in PBS though the tail vein and then scanned at different time points after injection of control IO, ATF-IO, or Cy5.5-ATF-IO using 3T MRI scanner as described above. Images from pre- and post contrast administration were compared to evaluate the efficacy of contrast enhancement by the target specific contrast agent. Region of interest (ROI) method was used to evaluate and quantify the contrast agent induced signal or T2 value changes in tumor and other organs. Signal of the leg muscle was used to normalize the signals in ROIs. T2 maps of MR images before and after contrast administration were calculated from fitting the data points at 8 different echo times ranging from 10 to 90 ms.

NIRF Optical Imaging of Mouse Mammary Tumors.

The tumor bearing mice was placed on special diet (Harlan Teklad, Madison, Wis.) to reduce background fluorescence for over two weeks. Before and at different time points following the injection of Cy5.5-ATF-IO or control IO nanoparticles, NIRF imaging of the tumor-bearing mice was taken using Kodak in vivo FX imaging system (Eastman Kodak Company, New Haven, Conn.). For each NIRF image, a corresponding X-ray image was taken to provide anatomic location of the tumor.

Histological Analysis.

Prussian blue iron staining was used to confirm the presence of IO nanoparticles in the tissue sections. Tumor and normal tissues were collected from the mice by the end of in vivo imaging experiments. About 5μ frozen tissue sections were incubated with Prussian blue staining solution containing a 1:1 mixture of about 5% potassium ferrocyanide and about 5% HCl acid for about 30 min at about 37° C. The slides were then rinsed and counterstained with nuclear fast red (Vector Laboratories, Burlingame, Calif.) for about 10 min.

Results

Development and Characterization of ATF-IO Nanoparticles:

Referring to FIG. 2, paramagnetic IO nanoparticles 210 with uniform sizes of about 4 to 30 nm were synthesized, which produced strong magnetic signals using the protocol as described in the experimental methods above. The results indicated that the size of nanoparticles/nanocrystals can be controlled by varying the heating time, the temperature, and the concentration of the precursors. After examination of magnetic properties of various sized IO nanoparticles, the IO nanoparticles 210 with a core size of about 10 nm size were selected to practice the present invention since these nanoparticles 210 combined characteristics of a relatively small particle size for in vivo tumor targeting, reasonable surface areas for conjugating biomolecules and sufficient T2 effect for MRI detection. To stabilize and functionalize surface of the IO nanoparticles 210, the nanoparticles 210 were coated with a layer 132 of amphiphilic polymers 220 grafted with carbon alkyl side chains 222, resulting water soluble IO nanoparticles with carboxyl side groups 222. The layer 132 in one embodiment was formed to have a thickness of about 2 nm. To reduce nonspecific binding and uptake by normal tissues, short PEG chains having about 3 to 4 PEG molecules were conjugated to the half of the carboxyl side groups 222 on the amphiphilic polymers 220. Inset 290 was a TEM image of the amphiphilic polymer coated nanoparticles 230. The magnetic signal of the amphiphilic polymer coated nanoparticles 230 in solution is further examined by MRI scans. The results 280 showed that the amphiphilic polymer coated 10 nM IO nanoparticles had strong paramagnetic T1 and T2 shortening effect with R1 (e.g., 1/T1)=3.6±0.3 mM-1·s-1 and R2 (1/T2)= 124±7.2 mM-1·s-1 at 3T, respectively.

Recombinant mouse ATF peptides produced from a pET bacteria expressing system were examined by gel electrophoresis and Western Blot analysis 240 to determine the amount and purify of the ATF peptides. Result of coomassie blue staining of the SDS-PAGE gel revealed a single ATF band located at about 18.5 KDa of the gel. To further confirm the presence of ATF peptides, Western Blot is performed using a monoclonal anti-histidine tag antibody. A strong positive band in the location corresponding to the ATF peptides identified by coomassie blue staining was found. Purified recombinant mouse ATF peptides 242, with or without labeled to a near infrared dye Cy5.5 244, were then conjugated to the IO nanoparticles 130 by crossing-linking the amine side groups of ATF peptides 242 to the carboxyl group on the surface of the IO nanoparticles 230 mediated by EDAC. After separation of unconjugated ATF peptides from the IO nanoparticles by column filtration, conjugation efficiency of ATF peptides to the active carboxyl groups of the IO nanoparticles was confirmed by two methods, including changes in the surface ζ potential of the nanoparticles and measurement of relative fluorescence intensity in fluorescence dye-labeled IO nanoparticles. It was found that the surface charge of nanoparticles before the conjugation was averaged at about −30 mV, however, reduced to about −11 mV after attachment of ATF peptides, suggesting that reduction of the carboxyl group on the surface of nanoparticles due to peptide conjugation. Additionally, when using Cy5.5-labeled ATF peptides, the conjugation efficiency was estimated by measuring the fluorescence intensity relative to the numbers of the IO nanoparticles. It was found that about 8 to 10 ATF peptides were attached to each IO nanoparticle using the conjugation method. Dynamic light scattering (DLS) measurement indicated that an assembled ATF-IO nanoparticle had a hydrodynamic diameter of about 53 nm.

Figure 3:
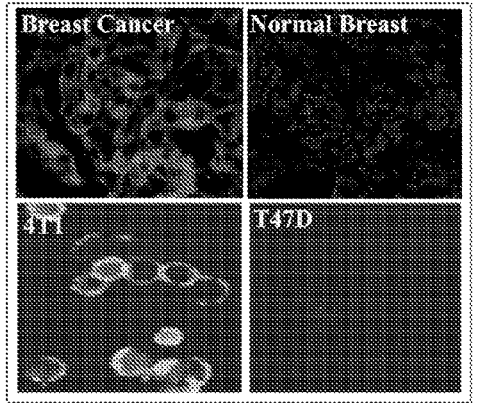
FIG. 3 shows the specificity of the ATF peptides or ATF-IO nanoparticles according to one embodiment of the present invention. A. Detection of uPAR expression by Immunofluorescence labeling. Using an anti-uPAR antibody, a high level of uPAR (red) was detected in frozen tissue section of an invasive human breast cancer tissue but was not detected in normal breast tissue obtained from the same patient (upper panel). Blue: Hoechst 33342 background staining. Surface-labeling of viable cells using anti-uPAR antibody and FITC-labeled secondary antibody showed a high level of uPAR in mouse mammary tumor 4T1 cells but not in human breast cancer T47D cells (green, lower panel). B. Determination of the specificity of recombinant ATF peptides and ATF-IO nanoparticles using a Pull-down assay. Lane 1: Free ATF peptides pulled down uPAR protein from 4T1 cell lysates; Lane 2: ATF-IO nanoparticles were also capable of binding and pulling down uPAR protein. Lane 3: control total lysates of 4T1 cells; Lane 4 and 5: uPAR protein band was not detected after incubation of free ATF peptides (lane 4) or ATF-IO nanoparticles (lane 5) with T47D cell lysates. C. Specific binding and internalization of Cy5.5-ATF-IO nanoparticles in uPAR expressing tumor cells. Cells growing on glass dishes were incubated with 20 pmol of ATF-IO nanoparticles for 3 hours at 37° C. After washing with PBS and fixed with ice-cold acetone, the dishes were examined under a confocal microscope. Intracellular localization of Cy5.5 fluorescence signal (red) is clearly seen in 4T1 cells but not in T47D cells (upper panel). Prussian blue staining further confirmed the presence of blue iron staining inside the 4T1 cells (lower panel).
Figure 3:
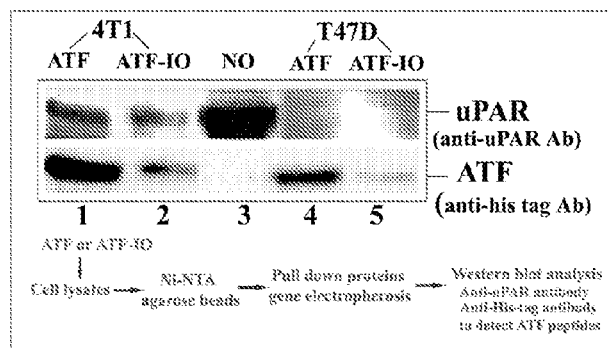
Figure 3:
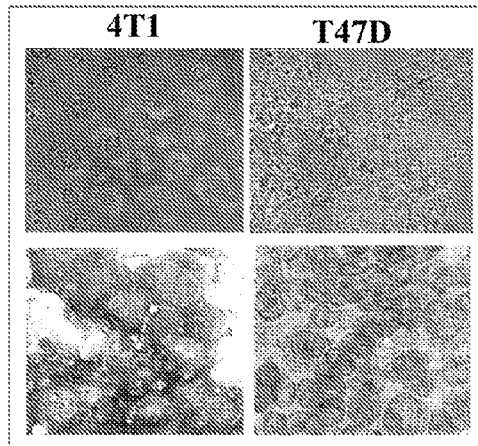

ATF-IO Nanoparticles Specifically Bind to and are Internalized by uPAR Expressing Tumor Cells:

First, the level of uPAR expression in human breast cancer and normal tissues were examined using immunofluorescence staining. Consistent with previous observations, uPAR was strongly positive in invasive breast cancer tissues but was not detected in normal breast tissues, as shown in FIG. 3A. A high level of surface uPAR was found in mouse mammary tumor 4T1 cells by immunofluorescence labeling of viable cells using an anti-uPAR antibody. However, human breast cancer T47D cells lacked uPAR expression (FIG. 3A). To determine if the ATF peptides maintain a high binding affinity after conjugated to the IO nanoparticles, a pull-down assay using cell lysates obtained from uPAR positive 4T1 and negative T47D cells was performed. Although it was shown that the binding of ATF to uPAR had species specificity, recombinant mouse ATF did cross-reacts with uPAR positive human cancer cells, such as breast cancer MDA-MB-231 and pancreatic cancer MIA PaCa-2 cell lines (Data not shown). The results showed that both unconjugated ATF and ATF-IO could bind to and precipitated down uPAR proteins in the cell lysates, resulting in a positive uPAR band detected by Western Blot assay in 4T1 cell lysates but not in T47D cell lysates, as shown in FIG. 3B. It was shown that interaction of uPA with uPAR led to internalization of the ligand/receptor complex. To determine whether the binding of ATF to uPAR induced the internalization process, Cy5.5-ATF peptides were conjugated to the IO nanoparticles (Cy5.5-ATF-IO). After incubation of Cy5.5-ATF-IO with viable 4T1 and T47D cells for abut 3 hr at about 37° C., the cells were examined under a confocal microscope. It was found that Cy5.5-ATF-IO nanoparticles specifically bound to and were internalized by uPAR expressing 4T1 cells but not by uPAP negative T47D cells, as shown in FIG. 3C. The presence of intracellular IO nanoparticles in 4T1 cells was further demonstrated by Prussian blue staining in FIG. 3C.

Figure 4:
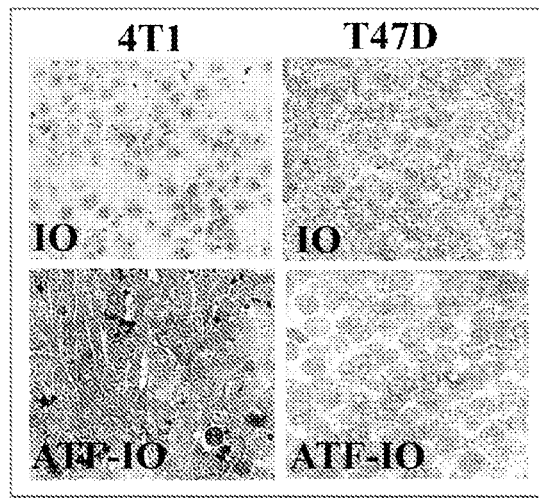
FIG. 4 shows MRI detection of magnetic signals in tumor cells after binding and internalization of the ATF-IO nanoparticles in vitro according to one embodiment of the present invention. A. Prussian blue staining shows specific binding and internalization of ATF-IO nanoparticles in 4T1 tumor cells after incubation at about 37° C. for about 3 hrs. Only few scattered blue staining found in 4T1 cells incubated with unconjugated IO or uPAR negative T47D cells incubated with either IO or ATF-IO nanoparticles. B. T2 relaxometry of MRI shows that specific binding and internalization of ATF-IO nanoparticles produces strong T2 contrast decrease in 4T1 cells (upper panel). A low T2 value indicates a high iron concentration (orange to red color). The result is further confirmed by changes in T2 values in 4T1 or T47D cells after incubation with ATF-IO or control IO nanoparticles using multi-echo $T_2$ weighted fast spin echo imaging sequences to collect a series of TE dependent data points. The fastest T2 value drop was detected in 4T1 cells incubated with ATF-IO nanoparticles (lower panel).
Figure 4:
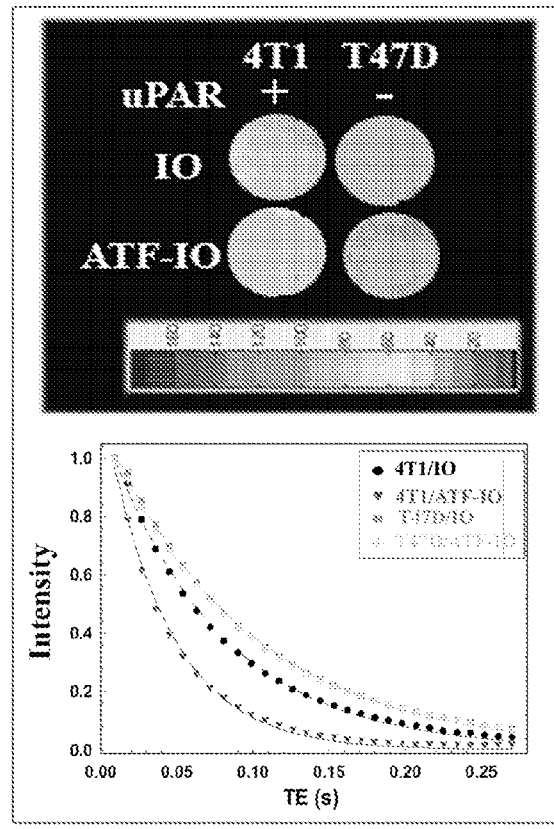

ATF-IO Nanoparticles Produce Strong Magnetic Signal Upon Binding to and Internalization by Tumor Cells In Vitro:

An important aspect of the present invention for the development of a receptor targeted molecular imaging probe is to accumulate sufficient amounts of contrast agents on the surface and inside cells that express a high level of receptors, which allow for the production of strong magnetic signal and contrast changes, and detection of receptor expressing cells by MRI. After incubation of unconjugated IO or ATF-IO nanoparticles with viable tumor cells, Prussian blue staining detected a high level of IO particles in 4T1 cells incubated with ATF-IO nanoparticles but not with unconjugated IO. uPAR negative T47D cells only showed a very low level of nonspecific uptake as shown in FIG. 4A. The cells were also collected and embedded in agarose for MRI scans. A T2 value of each sample was calculated from obtained MR images to generate a T2 map. Cell plate phantom with 4T1 cells and ATF-IO nanoparticles showed IO nanoparticle-induced MRI contrast with significant signal drops in T1 and T2 weighted gradient echo imaging, as shown in FIG. 4B (upper panel). $T_2$ relaxometry indicated that the T2 value of 4T1 cells with IO-ATF nanoparticles dropped significantly compare to the T47D cells with ATF-IO nanoparticles and the samples treated with unconjugated IO nanoparticles, as shown in FIG. 4B (lower panel). Since T2 value is the function of iron concentration, T2 relaxometry data suggested that T2 weighted MRI contrast is induced by the specific binding of ATF-IO nanoparticles to the uPAR expressing 4T1 cells.

Figure 5:
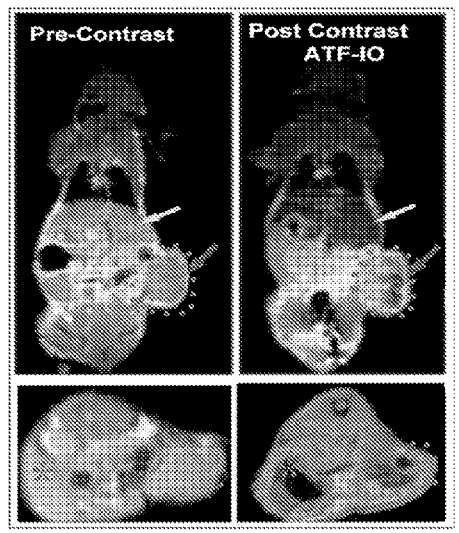
FIG. 5 shows in vivo MRI of a 4T1 mammary tumor using ATF-IO nanoparticles according to one embodiment of the present invention according to one embodiment of the present invention. A. MRI of an s.c. mammary tumor. ATF-IO nanoparticles were injected into the Balb/c mouse bearing an s.c. 4T1 mammary tumor for about 6 hrs. MRI Scanning was performed as described in the methods, and pre- and post-contrast MR images were collected. A marked T2 contrast decrease was detected in s.c. tumor areas (pink dash-lined). It seemed that intratumoral distribution of ATF-IO nanoparticles was not uniformed since the strongest T2 effect was seen in peripheral side of the s.c. tumor (red arrow). T2 contrast change was also found in liver (yellow arrows and Pink *). This mouse MRI scanning image was a representative image of seven mice that received ATF-IO nanoparticles. The MRI image of mice received unconjugated IO was shown in FIG. 6B. B. Organ specific profiling of MRI signal change. T2 intensity changes in the mouse received IO or ATF-IO nanoparticles for about 6 hrs were measured in the regions of tumor or various normal tissues. Relative intensity was calculated using the intensity in the leg muscle as 1. Fold decreases of the intensity in MR image were compared between pre- and post-ATF-IO injection and plotted in this figure. The Bar figure represented mean-values of three regions. C. Examination of tissue distribution of the IO nanoparticles in tumor and normal tissues about 48 hrs after the particle injection by Prussian blue staining. Blue iron staining positive cells were found in tissue sections of the s.c. tumor obtained from a mouse that received ATF-IO nanoparticle injection. It was clear that the tumor areas with a high percentage of blue cells were those near the tumor boundary. High magnification images shows that blue iron staining was likely located in the cytoplasm of the cells. On the other hand, s.c. tumor sections obtained from a mouse received the tail vein injection of unconjugated IO do not have detectable positive cells. 4T1 mammary tumor model also gives rise to spontaneous lung metastases. Although a T2 contrast change was not detected in the lung due to an intrinsic low contrast in MRI of the lung, the presence of lung metastasis was obvious in the excised lung tissues (pink arrow). Prussian blue staining of tissue sections containing lung metastases shows a high percentage of iron positive cells, suggesting that ATF-IO nanoparticles could also target lung metastases. In normal tissue sections, large amounts of iron positive cells were detected in the liver and spleen. However, a marked lower level of iron positive cells was found in the liver and spleen of the mouse injected with ATF-IO nanoparticles. Control sections were from the liver and spleen of normal mouse, which show a low level of iron staining in normal spleen tissue. Iron staining positive cells were not detected in the heart and brain after injection either IO or ATF-IO nanoparticles. The majority of tissue sections from the lung and kidney do not have iron positive cells in IO or ATF-IO injected groups. Occasionally, a few scattered iron staining positive cells were detected in tissue sections. Red: background staining with nuclear fast red.
Figure 5:
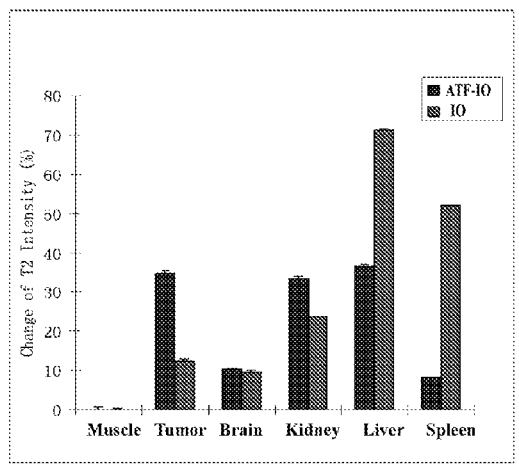
Figure 5:
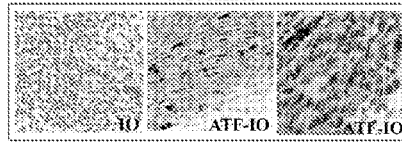
Figure 5:
Figure 5:
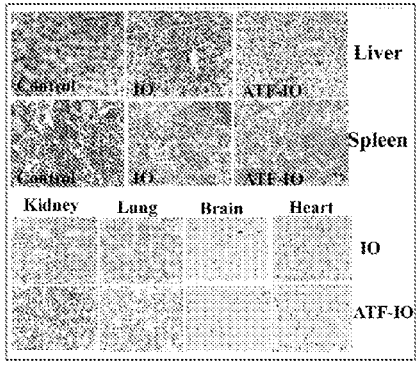

In Vivo Targeting and MR Imaging of Subcutaneous Mammary Tumors in Mice:

First, the ability of specific targeting and MR imaging of subcutaneous (s.c.) tumors was estimated using a mouse mammary tumor model derived from 4T1 tumor cell line. ATF-IO nanoparticles were administrated via the tail vein into Balb/c mice bearing s.c 4T1 tumors. Result of $T_1$ weighted FLASH imaging and T2 weight fast spin echo imaging showed that ATF-IO nanoparticles were selectively accumulated in s.c. tumors, evidenced by $T_2$ effect induced MRI signal decreases in various areas of the tumor mass, as shown in FIG. 5A. The region of interest analysis of MRI signal change showed that the level of MRI signal in the tumor post injection of ATF-IO particles reduced three-folds as compared to tumor MR images from mice received unconjugated IO particles (FIG. 5B). Although decreases in MRI signal was observed in liver and spleen in ATF-IO injected mice due to IO particle-induced T2 effect, the reduction of MRI signal was 50% (liver) to 80% (spleen) less than that of the mice that received unconjugated IO nanoparticles, suggesting that liver and spleen uptake of the nanoparticles were reduced using ATF-IO nanoparticles, as shown in FIG. 5B. To further confirm the distribution of unconjugated or ATF-IO nanoparticles in normal and tumor tissues, Prussian blue staining was performed on the frozen tissue sections obtained from the mice that received control IO or ATF-IO nanoparticles. Blue stained cells were detected in the tumor sections of ATF-IO injected mice but not in the unconjugated IO sections. High magnification images showed intracellular localization of the IO nanoparticles in the cells, as shown in FIG. 5C. It is well known that s.c. 4T1 mammary tumor model produces spontaneous lung metastases. It was also found that Prussian blue positive cells in tissue sections of the lung metastases obtained from a mouse that received the tail vein injection of ATF-IO nanoparticles, as shown in FIG. 5C. In normal tissues, it was found that high levels of Prussian blue positive cells in the liver and spleen of the mice received unconjugated IO injection. However, liver and spleen tissue section from the ATF-IO mouse group had less positive cells. IO nanoparticles in tissue sections of the brain and heart obtained from mice injected with either unconjugated IO or ATF-IO nanoparticles, were not detected, as shown in FIG. 5C. For both ATF-IO and IO nanoparticle injected groups, the lung and kidney tissues were negative in most cases (FIG. 5C) and only a few scattered iron staining positive cells were detected in some of the tissue sections.

Figure 6:
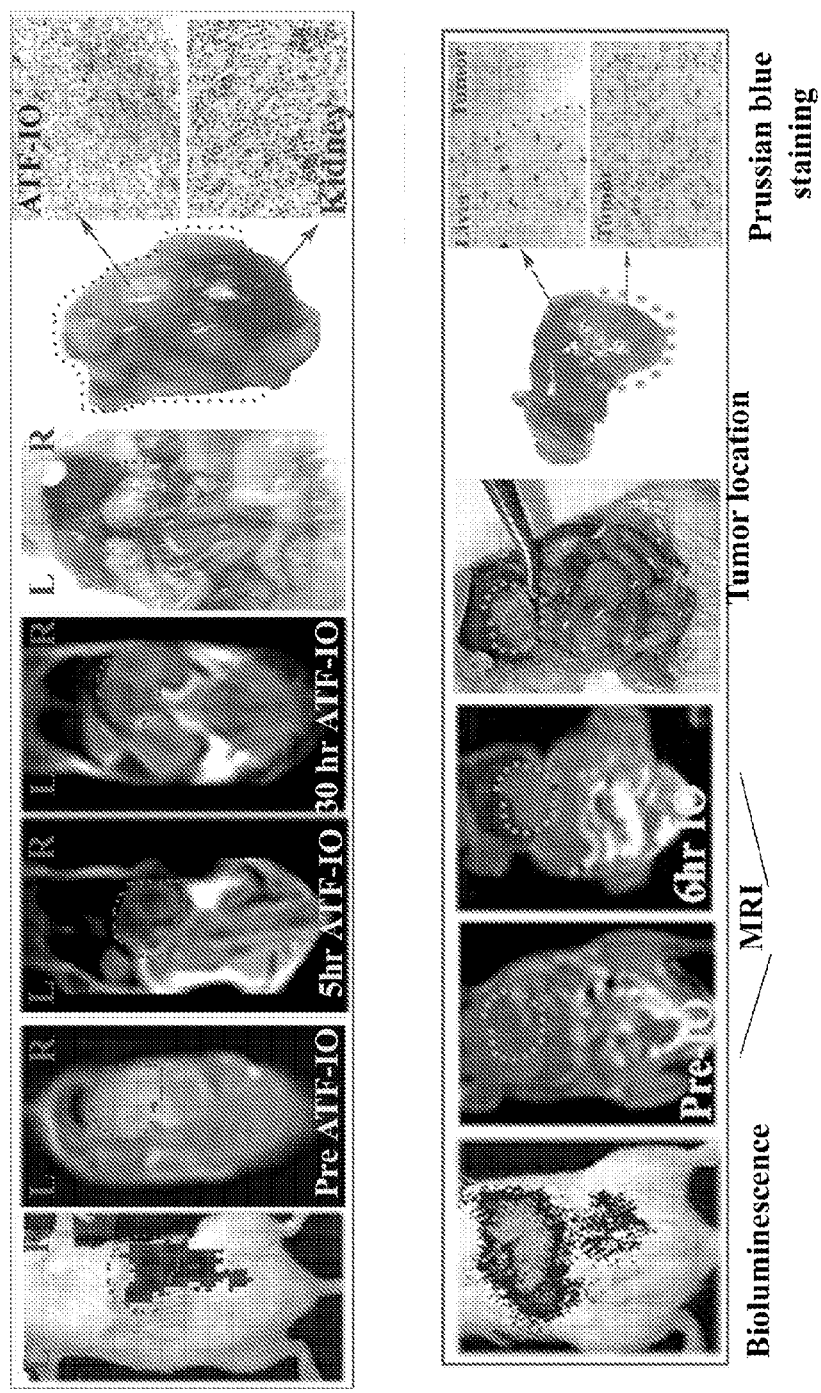
FIG. 6 shows targeting and in vivo MR tumor imaging of intraperitoneal mammary tumor lesions after systemic delivery of ATF-IO nanoparticles according to one embodiment of the present invention. Upper panel: 10 days after injection of luciferase gene stable 4T1 cells, bioluminescence imaging confirmed the presence of intraperitoneal tumors on the upper right of the peritoneal areas. About 5 or 30 hrs after the tail vein injection of about 0.28 mmol of ATF-IO nanoparticles, a significant T2 signal drop was detected in upper right areas, corresponding to the bioluminescence imaging. MRI reveals two areas with strong T2 contrast decrease located near the right kidney (red dash-lined). After sacrificing the mouse, two tumor lesions were found on the top of the right kidney, which correlated very well with the tumor location detected by MRI. Specific accumulation of ATF-IO nanoparticles in the tumor tissues was demonstrated by Prussian blue staining. Lower panel: A control mouse with a tumor lesion in the upper right of peritoneal cavity received unconjugated IO nanoparticles for about 6 hrs. There was no MRI contrast change in the tumor area (pink dash-lined), while the liver of the mouse shows a marked contrast decrease. Prussian blue staining of tissue sections showed that there was no blue iron staining positive cells in the tumor tissues. However, the normal liver tissue near the tumor region was positive for the iron staining (A red-dash line divides normal liver and tumor tissues).

Targeted MR Imaging of Intraperitoneal Mammary Tumor Lesions Using ATF-IO Nanoparticles:

To determine the feasibility of targeting and in vivo imaging of metastatic lesions, ATF-IO nanoparticles were injected into the tail vein of a mouse bearing intraperitoneal (i.p.) 4T1 tumors stably expressing a firefly luciferase gene. The presence of tumor lesions was determined by bioluminescence imaging (BLI). At about 5 hrs after the ATF-IO particle injection, a marked T2 contrast decrease was detected on the upper right of the abdomen, which delineates nicely the margin of two tumor lesions on the top of the right kidney (FIG. 6, upper panel). MR image after about 30 hrs showed slight increase in T2 contrast compared to that of about 5 hrs but the T2 effect in the tumor lesions were still visible. However, such a T2 signal change was not detected in a mouse bearing a tumor mass below the left lobe of the liver at about 6 hrs after the tail vein injection of unconjugated IO (FIG. 6, lower panel). The selective accumulation of the ATF-IO nanoparticles in metastatic i.p. tumor lesions was further demonstrated by Prussian blue staining, showing a high percentage of iron positive cells in the tumor lesion while the normal kidney beneath the tumor was totally negative. (FIG. 6, upper panel). On the other hand, iron positive cells were not detected in tissue sections of the i.p. tumor mass obtained from the mouse that received unconjugated IO injection, while the adjacent normal liver tissue has a high level of iron positive cells (FIG. 6, lower panel).

Figure 7D:
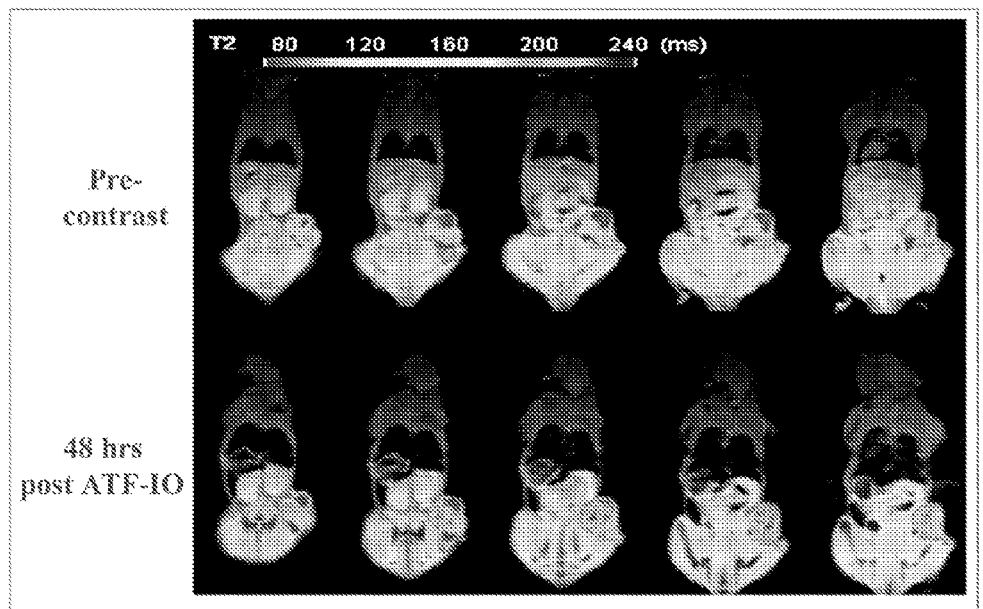
FIG. 7 shows dual modality imaging of an s.c. 4T1 mouse mammary tumor using Cy5.5-ATF-IO nanoparticles according to one embodiment of the present invention. A. Real time NIRF optical imaging of tumor targeting and tissue distribution of Cy5.5-ATF-IO nanoparticles after the tail vein injection. A nude mouse bearing an s.c. 4T1 tumor received the tail vein injection of about 0.2 nmol of Cy5.5-ATF-IO nanoparticles. NIRF optical imaging was performed at different time points using Kodak FX in vivo imaging system equipped with a filter set with an excitation wavelength of about 625 nm and emission wavelength of about 700 nm. NIRF signal was detected in the peripheral tumor areas about 24 hrs after the injection (light purple dash lined). The signal gradually increases and moves toward the center of the tumor mass, reached to the strongest level at about 72 hrs after the particle injection. However, NIRF signal decreases after about 80 hrs. Additionally, NIRF signal was also found in the kidney areas, suggesting that breaking-down components of Cy5.5-ATF-IO or even intact Cy5.5-ATF-IO may be eliminated through the kidney. B. Simultaneous MR and optical imaging of a mammary tumor. Tumor-bearing mouse that received the tail vein injection of Cy5.5-ATF-IO nanoparticles for about 48 hrs showed T2 signal drop in the low left half of the s.c. tumor in T2 weighted MR image. Optical imaging reveals the NIRF signal in the tumor area corresponding well with the MRI results (light purple dash lined). Neither T2 contrast change nor optical imaging was detected in the s.c. tumor of the mouse that received unconjugated IO nanoparticles. MRI shown represents the results of a total of seven control tumor bearing mice received IO nanoparticles. C. Histological analysis of tumor tissues. Examination of the location of ATF-IO nanoparticles and Cy5.5 signal in tumor tissues. Prussian blue staining was conducted in frozen tissue sections of the tumor. Some of the sections were doubly labeled with Alexa Fluor 488-anti-CD68 antibody, a marker for macrophage. Many blue iron positive cells were negative for CD68 (red arrow), suggesting that intratumoral accumulation of ATF-IO was not due to non-specific uptake of ATF-IO by macrophages. Moreover, co-localization of blue iron staining and Cy5.5 signal was also detected in the tumor tissues (white arrows). D. T2 map of a series of MR images taken from an s.c. mammary tumor lesion. Multi-echo $T_2$ weighted spin echo imaging using 3D-MRI reveals intratumoral distribution of ATF-IO nanoparticles throughout different levels of tumor mass. Orange to red colors represents tumor areas with the most T2 contrast decreases, indicating that accumulation of ATF-IO nanoparticles in a particular tumor area. Regional of interest T2 mapping was used.

Dual Modality Tumor Imaging Using 4T1 Mouse Mammary Tumor:

Conjugation of Cy5.5 dye-labeled ATF peptides to IO nanoparticles provides one with an additional optical imaging capacity to this nanoparticle, allowing for simultaneous tumor imaging using both sensitive NIRF optical and high resolution MR imaging. Importantly, it also provides means to monitor the distribution of ATF-IO nanoparticles in tumor and normal tissues in vivo in real time. The changes of NIRF signals were examined in mice bearing s.c. 4T1 tumors at different time points after the tail vein injection of Cy5.5-ATF-IO or control unconjugated IO nanoparticles. It was found that the level of NIRF signal could be detected clearly in the peripheral area of the tumor mass about 24 hrs after the particle administration. The intensity of NIRF signals gradually increased to the peak level between about 48 to 72 hrs. It seemed that the ATF-IO nanoparticles also entered into the center tumor areas in those time points (FIG. 7A). The intensity of NIRF signal in the tumor started to decline at about 80 hrs. NIRF signal was also detected in the kidneys and bladder, suggesting that free Cy5.5, conjugated Cy5.5-ATF, or even Cy5.5-ATF-IO may be eliminated through the kidney. To determine the correlation of optical and MR images of the tumor, MRI scan was performed on the same mouse. Results of MRI showed T2 contrast decrease at the lower-left portion of the tumor mass, which correlates well with the location of optical signal (FIG. 7B). However, MR image of the mouse that received the tail vein injection of unconjugated IO did not show T2 contrast change in the s.c. tumor. NIRF optical signal was not detected in this tumor (FIG. 7B). Examination of the location of Prussian blue staining and Cy5.5 signal positive cells in the tissue section of the tumor demonstrated co-localization of both the IO nanoparticles and Cy5.5 signal in the same cell population of the tumor cells (FIG. 7C). This result also suggests that the Cy5.5-ATF-IO nanoparticle is stable in vivo and remains to be an intact nanoparticle to bind and to be internalized together by tumor cells. Previous studies reported that IO nanoparticles can be non-specifically taken in by macrophages. To determine which type of the cells contains the IO nanoparticles in the tumor, the tumor tissue sections were stained with both Prussian blue and an antibody to CD68, a marker for macrophages. It was found that Prussian blue positive cells are present in both CD68 positive and negative cell populations. A high percentage of Prussian blue positive cells do not express CD68, suggesting that non-macrophage cell type, such as tumor cells, contain IO nanoparticles. It has been shown that active macrophages also express a high level of uPAR. It is highly likely that the presence of iron positive macrophages may be due to active targeting uPAR expressing macrophages rather than non-specific uptake of IO particles, since Prussian blue positive cells were not found in the tumor of the mice received unconjugated IO nanoparticle injection.

Compared to optical imaging, MRI has a high resolution and three-dimensional imaging capacity which enables one to precisely evaluate the intratumoral distribution of IO nanoparticles. Results from examination of T2 map derived from multi-echo $T_2$ weighted spin echo imaging of an s.c. mammary tumor showed that accumulation of ATF-IO nanoparticles was not uniformly distributed inside the tumor mass. At various levels of tumor MR images, region of T2 contrast decreases were located in different tumor areas (FIG. 7C). Interestingly, the areas with the most T2 contrast decrease were largely in the periphery regions of the tumor where the tumor area enriches in blood vessels, relative to the necrotic areas at the center of the tumor.

Discussion

Molecular imaging probes targeting specific biomarkers on tumor cells have been long sought-after in applying molecular imaging for cancer detection and personalized therapeutics. However, the development of receptor targeted imaging and its in vivo applications are hindered by the obstacles including: 1) the identification of cell surface biomarkers that are expressed in a high percentage of tumor cells in the majority of tumor types; 2) the production of stable and high affinity targeting ligands in sufficient quantity for chemical modification, conjugation and in vivo animal studies; and 3) the development of safe and biodegradable contrast agents emitting strong imaging signal.

The uPAR targeted IO nanoparticle imaging probes according to the present invention provides an example of addressing those challenges and demonstrates the feasibility of in vivo receptor targeted tumor imaging. The results show that ATF-IO nanoparticles are capable of targeting uPAR expressing tumor cells in vitro and in vivo. Selective accumulation of the ATF-IO or Cy5.5-ATF-IO nanoparticles in the tumor lesions produces strong contrast changes for tumor imaging using MR and optical imaging approaches. The tumor imaging obtained using ATF-IO nanoparticles results from several unique features of the nanoparticles. First, a tumor targeting ligand from the receptor binding domain of uPA is used, which is a natural high affinity ligand for uPAR. uPA includes three independently folded domain structures: growth factor domain (GFD), Kringle domain, and serine protease domain. Enzymatic digestion of uPA by plasmin generates an ATF, including GFD and Kringle domains, and the low molecular weight fragment serine protease domain. uPA binds to uPAR with a high affinity through the GFD of ATF (Kd=0.28 nm). Additionally, the ATF (residues 1-135 aa) of uPA is also a potent uPA binding antagonist to uPAR. Systemic or local delivery of ATF peptides using an adenoviral vector or conjugated to a protein carrier prevents the formation of the uPA/uPAR complex and inhibits tumor growth and angiogenesis. Importantly, interaction of uPA with uPAR leads to the internalization of the ligand/receptor complex, suggesting an advantage of targeting uPAR for tumor imaging and drug delivery. By cloning the gene sequence of ATF to a bacterial expressing plasmid, one can produce large scale of the recombinant protein using the standard protein engineering method in the laboratory, which enables one to conduct in vivo study in animal tumor models. The above results reveal that recombinant ATF peptide maintains its binding affinity with uPAR. Even after being cross-linked to the surface of the IO nanoparticles, it can still bind to uPAR protein in solution and on the cell surface, evidenced by specific pull down uPAR proteins in tumor cell lysates, binding to and internalized by uPAR positive but not uPAR negative control cells in vitro. This exemplary embodiment of the present invention was practiced using mouse ATF peptides and 4T1 mouse tumor model to evaluate the feasibility of targeting uPAR. The interaction of uPA with its receptor is specific to species. A major advantage of using mouse ATF peptides to practice the present invention in a mouse tumor model is that the targeting specificity, sensitivity and biodistribution in normal tissues of this imaging probe can be evaluated in greater details. Although a cross reactivity of the recombinant mouse ATF peptides to uPAR expressing human tumor cells was observed, mouse tumor cells still showed a higher reactivity compared to human cells.

The uPAR is highly expressed in a high percentage of tumor cells in many types of human cancers. The level of the receptor expression and its correlation with an aggressive cancer type, the presence of distant metastasis and a poorer prognosis has been studied extensively in breast cancer, showing that human breast cancer cells have 130,000 to 500,000 uPAR per cell while primary normal human mammary epithelial cells only have 2,500 uPAR per cell. Such a high level of receptor over expression in the tumor cells makes the uPAR a suitable target for molecular MR imaging of breast cancer. The highest level of uPAR expression is detected in the invasive edge of the tumor regions, where usually have high blood vessel intensity, making it accessible for the targeted IO nanoparticles to uPAR expressing cells. The results of both NIRF optical and MR imaging as well as Prussian blue staining of tumor tissue sections obtained from the mouse that receives ATF-IO nanoparticles shows that the IO nanoparticles are preferably accumulated in the tumor cells close to the tumor burden areas. Since the binding of ATF peptides to uPAR results in internalization of ATF-IO nanoparticles, increasing the amounts of intracellular IO particles could further enhance imaging signals.

Additionally, the high quality and uniform size IO nanoparticles produce a strong MR contrast. Studies of size effects of paramagnetic IO nanoparticles on MR signals, show that the T2 effect becomes stronger as the size of the IO nanoparticles gets larger. The size uniformed and amphiphilic copolymer coated IO nanoparticles disclosed in the present invention exhibit high magnetism with $T_2$ of 124 $mM^{-1} \cdot S^{-1}$ at a about 10 nm core size using the field strength of 3T, which is a much stronger contrast effect than many other IO nanoparticle formulation used in the conventional approaches. Amphiphilic copolymer adapted for coating the surface of the IO nanoparticles is thin (estimated at ~2 nM) and very stable, which not only provides a functionalized surface for conjugating tumor targeting ligands but also forms a strong core-shell protection for the IO core particle. The in vivo imaging results suggest that this type of IO nanoparticles are stable in vivo and in intracellular environments for over about 48 hrs since strong MR and NIRF optical imaging signals can be detected at this time point.

Compared to dextron or PEG coated IO nanoparticles used in the conventional approaches, amphiphilic copolymer coated IO nanoparticle is a relatively small particle complex that is desirable for in vivo delivering into the tumor mass. Although some other small molecule imaging agents may have a better intratumoral distribution compared to nanoparticle-based imaging agents, those imaging agents are usually eliminated from blood circulation in short time (less than 30 min), which makes it hard for targeted contrast agents to accumulate sufficient amounts for sensitive detection of cancers. However, the polymer coated IO nanoparticles according to the present invention have over about 8 hrs of plasma retention time when introduced intravenously. This allows the targeted IO nanoparticles to have enough time to reach the tumor sites for binding to and being internalized by tumor cells. It is also observed that intratumoral NIRF signal increases at the longer time points and reaches to the highest level around 48 to 72 hrs after the tail vein administration of IO nanoparticles, suggesting that long blood retention time may facilitate the tumor targeting process by the nanoparticles. Examination of tumor tissue sections obtained from mice received either ATF-IO or unconjugated IO shows that the presence of the IO nanoparticles in the tumor is the result of active targeting tumor cells rather than the passive targeting through leaky tumor vessels or non-specific uptake by tumor macrophages. Additionally, Prussian blue positive cells are detected in the tumor from the mice that receive ATF-IO nanoparticles but not in tumor from the mice that receive unconjugated IO particles using the amount of IO nanoparticles recited in the example. However, in a separate study using an orthotopic human pancreatic cancer model xenografted in nude mice, a few Prussian blue positive cells are found in the tumor area obtained from the mouse received two-fold higher amounts of unconjugated IO nanoparticles, suggesting that the amount of nanoparticles administrated into mouse may affect tumor targeting. In addition, several other factors may also contribute to the results, including that the ATF-peptide-conjugated IO is smaller than antibody conjugated QDs reported by Gao et al. [3], and that longer time points for tumor imaging and examination of tumor tissues which allow for the unbound IO nanoparticles to be cleared out of the tumors. Although ATF-IO nanoparticles are found in CD68 positive macrophages, actively targeting plays a role since Prussian blue positive cells are not found in tissue sections of the tumors from mice received unconjugated-IO, which should have a similar amount of intratumoral macrophages as seen in the tumors of ATF-IO group. It is shown that uPAR is also upregulated in several types of tumor-associated stromal cells, such as macrophages, endothelial cells and fibroblasts. According to the present invention, ATF-IO nanoparticles are able to actively targeting those cell populations in human pancreatic cancer xenograft model. Targeting tumor cells as well as tumor stromal cells enhances the sensitivity of tumor imaging.

Although the production of dual modality IO nanoparticles by direct conjugation of Cy5.5 to the surface coating of IO has been reported previously, but no one suggested or even hinted to apply Cy5.5 dye-labeled ATF-peptides for conjugation to IO nanoparticles so that the results of optical imaging and tissue distribution are not affected by non-specific signals generated from possible unconjugated IO nanoparticles present in the ATF-IO preparation, as disclosed in the present invention. It is well known that MRI has a great tissue penetration, high resolution and 3-D imaging capacity but it is not a very sensitive imaging approach. Addition of a near infrared dye Cy5.5 to ATF-peptides not only provides means to quantify the amount of conjugated peptides on the IO nanoparticles but also produces strong NIRF signals for real-time imaging and sensitive detection of tumor targeting ability and tissue distribution of the ATF-IO nanoparticles in vivo. Therefore, Cy5.5-ATF-IO nanoparticles can be utilized as dual modality imaging nanoprobes that combine advantages of both NIRF optical and MR imaging, for detection of a breast cancer.

It has been reported that large portions of IO nanoparticles are taken up by reticuloendothelial system in the liver and spleen, and then are subsequently for iron storage or utilization via metabolism. However, systemic delivery of the ATF-IO nanoparticles leads to accumulation of the IO nanoparticles at the tumor site while reducing liver and spleen uptake. This suggests that conjugation of ATF-peptides to the nanoparticles prevents or hinders non-specific retention of the nanoparticles in the liver and spleen, where are the common organ sites for enrichment of many types of non-targeted nanoparticles after systemic delivery. Results from the real-time optical imaging also suggests that some ATF-IO nanoparticles trapped in liver or spleen non-specifically may return to blood circulation and then target to tumors since stronger optical signal is consistently observed for about 48 hrs after the tail vein injection of the IO nanoparticles. Furthermore, MRI contrast change in the tumor also appears hours after the tail vein administration of the ATF-IO nanoparticles. When tracking signal change at different time points, it is found that MRI signal decreases in liver and spleen at the first hour in T1 weighted gradient echo imaging and T2 weighted fast spin echo imaging and followed by the signal drops in the area of tumor after 6 hours, which lasted more than 48 hours.

From examination of MR images and histological analysis of tissue sections, it is noticed that ATF-IO nanoparticles are not uniformly distributed in the tumor mass. The results of Prussian blue staining show that single dose administration of ATF-IO nanoparticles results from about 15 to 30% of IO positive cells in the tumor tissues. In general, the percentage of IO positive cells is higher in intra-peritoneal tumors compared subcutaneous tumors, which may be due to a low blood vessel density inside large subcutaneous tumors. Although the strength of the imaging signals generated from those cells is sufficient for detecting contrast changes by MRI or by optical imaging, optimal amounts of ATF-IO nanoparticles and times of administration are determined so as to increase intratumoral distribution of the IO nanoparticles while retaining the targeting specificity.

In sum, the exemplary embodiment of the present invention, among other things, has demonstrated an uPAR targeted molecular imaging nanoprobe that selectively binds to and is internalized by tumor cells. Unique features of this nanoprobe includes an uniform size core, a thin amphiphilic copolymer coating, and a high affinity receptor binding domain of uPA conjugated with a near infrared dye. This targeted nanoprobe is specifically accumulated at the primary and metastatic tumor lesions, allowing for in vivo MR and optical imaging in a mouse mammary tumor model. Therefore, production of uPAR-targeted imaging nanoparticles is a promising approach for the development of novel molecular imaging approach for the detection of the breast cancer.

Example 2

Peptide Conjugated IO Nanoparticles for Targeted MR Imaging and Therapy of Pancreatic Cancer Experimental Methods Preparation of IO Nanoparticles with Functionalized Surface:

IO was prepared by heating iron oxide powder and oleic acid in octadecene over 315° C. The size of IO was tuned through changes such as heating time, temperature, and concentration of the iron oxide and oleic acid [14]. IO nanoparticles with highly uniformed core sizes of 9 or 10 nm were used for this example. Amphiphilic polymers were coated to the surface to convert hydrophobic IO nanoparticles to stable, water soluble and biocompatible nanoparticles. The hydrocarbon chains of the polymer intercalate into the inner hydrophobic layer that stabilize IO nanoparticle surface while carboxylic acid groups in the out-layer make the IO nanoparticles hydrophilic and reactive for conjugating proteins, peptides or small molecules.

Engineering Tumor Targeted-IO Nanoparticles:

A 135-amino acids of the ATF of mouse uPA, which contains a receptor binding domain but lacks a catalytic domain of uPA, was produced in a bacteria-expressing system using a plasmid construct with an ATF gene and 6× his-tag (cloned in the laboratory). A plasmid construct containing a ScFvEGFR single chain antibody gene was produced and the protein was expressed in bacteria-expressing system. Recombinant proteins were purified using Ni-columns. 17 KD ATF peptides or 25 KD ScFvEGFR single chain antibodies were conjugated to the nanoparticles via carboxyl groups after activation with EDAC to form ATF-IO or ScFvEGFR-IO. An estimated ratio of 10 protein molecules per IO nanoparticle was used for the conjugation.

Examination of Specificity of the Targeted-IO Nanoparticles Using MRI Scans or Prussian Blue Staining:

Human pancreatic cancer cell line MIA PaCa-2 (from ATCC) was incubated with unconjugated, ATF-, ScFvEGFR- or control GFP-IOs for about 2 hrs. After washing, the cells were examined by Prussian blue staining or embedded in 1% agorse gel plate for MRI T2 measurement to determine specificity of the IO nanoparticles. T2 measurements of IO-labeled cells was accomplished using T2 weighted fast spin echo sequence with variable echo times (TEs). T2 values of cell plates were calculated from images collected at various TEs to obtain maps of T2.

Cell Proliferation Assay:

To determine the effect of blocking uPAR by ATF or EGFR by ScFvEGFR on proliferation of pancreatic cancer cells, MIA PaCa-2 cells were plated in 96-well plates and incubated with unconjugated, ATF-, or ScFvEGFR-IO for about 48 hrs. The percentage of viable cells was determined by MTS Cell Proliferation Assay. Cell images were taken using a microscope.

Examination of Specificity and Tissue Distribution of the Targeted-IO Nanoparticles:

An orthotopic pancreatic tumor xenograft model was established in athymic nude mice by surgically implanting MIA PaCa-2 cells into pancreas. Under anesthesia, $5 \times 10^6$ of the cells were injected directly into pancreas. For several weeks after the cell implantation, MRI scan was performed on each mouse to obtain images prior contrast administration as control. Unconjugated control agents, ScFvEGFR- or ATF-IO nanoparticles (about 200 μg each) were then injected through the tail vein and MRI scan was performed on mice using a 3T scanner and a 5-cm wrist coil. Typical image parameters were: filed of view (FOV) of 110 mm, imaging matrix of 256×146 and 40 slices with 1.2 mm slice thickness without slice gap in the coronal section, TE of 10 ms, TR of 350 ms for T1 weighted spin echo imaging or TE of 2.6 ms. To examine the retention of contrast agent, mice were scanned at the different time points post IO-nanoparticle administration.

Results

Figure 8:
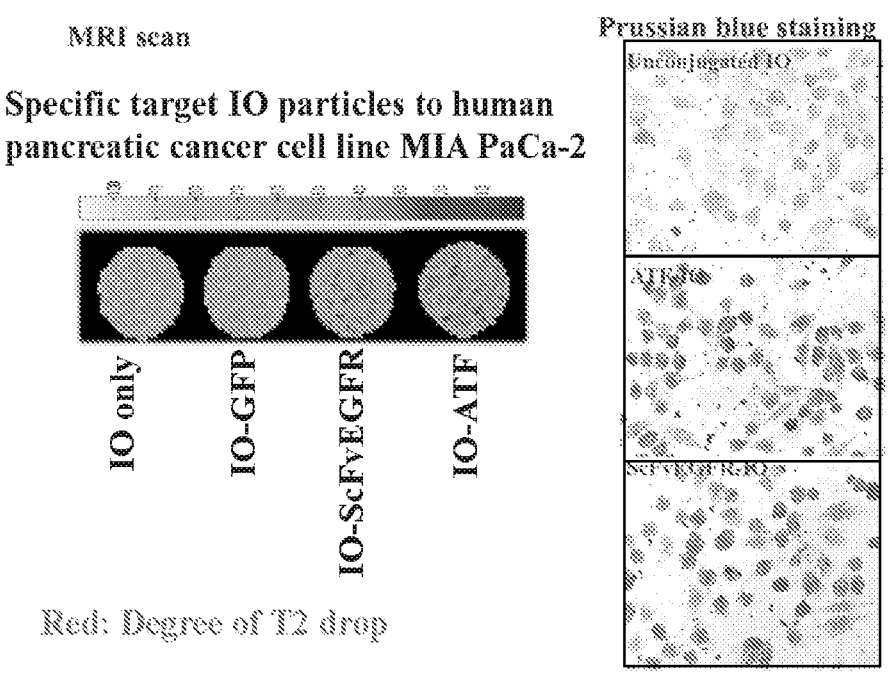
FIG. 8 shows according to one embodiment of the present invention specific binding of the targeted-IO nanocrystals to pancreatic cancer cells detected by MRI scan or Prussian blue staining. For MRI scans, MIA PaCa-2 cells were incubated with various IO nanoparticles for about 2 hrs. After washing, the cells were embedded in 1% agrose and analyzed by MRI scan as described in the Method. Red colored signals represented cell clusters bound to the targeted-IO particles and displayed reduced T2 signals. Prussian blue staining on cells growing in chamber slides was performed according to a standard protocol. A strong blue iron staining was found inside the cells incubated with ATF- or ScFvEGFR-IO while unconjugated-IO treated cells only showed a weak non-specific uptake of the IO particles.

Targeted IO Nanoparticles Exhibit Specific Binding to Pancreatic Cancer Cells:

Both ATF- and ScFvEGFR-IO nanoparticles were able to bind and be internalized by human pancreatic cancer cells. After incubating with MIA PaCa-2 cells, ATF- or EGFR-IO nanoparticles specifically bound to MIA PaCa-2 cells evidenced by significantly shortened T2 in ATF-IO or ScFvEGFR-treated cells but not in IO nanoparticle or GFP-IO nanoparticle-treated cells (FIG. 8A). Specific binding and internalization of ATF- or ScFvEGFR-IO nanoparticles were further confirmed by Prussian blue staining (FIG. 8B). Although previous reports suggested that there is species specificity in binding uPA to its receptor, it was found that recombinant mouse ATF peptides were able to bind to uPAR positive mouse and human cancer cells.

Figure 9:
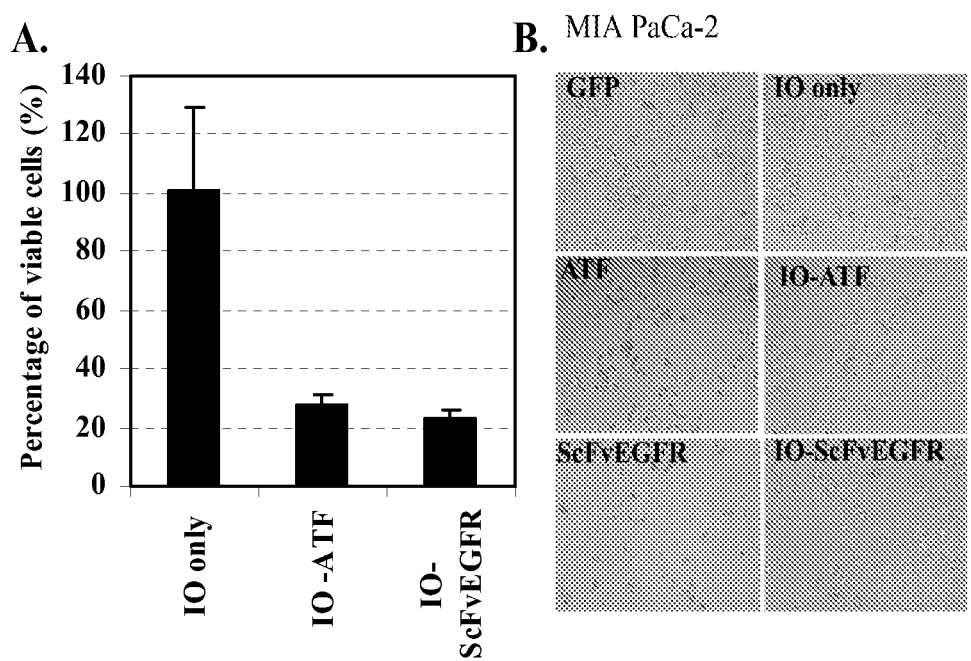
FIG. 9 shows according to one embodiment of the present invention inhibition of cell proliferation and/or induction of cell death after treating human pancreatic cancer cells with free ATF and ScFvEGFR peptides or IO-conjugated peptides. A. MTS cell proliferation assay. B. Representative areas of cell images 48 hrs after treatment.

ATF and SvFcEGFR Inhibit Proliferation of Human Pancreatic Cancer Cells:

To determine whether ATF and ScFvEGFR could block function of their receptors and inhibit growth of tumor cells, the effect of ATF- or ScFvEGFR-IO nanoparticles on MIA PaCa-2 cells were examined in vitro. It was found that incubation of the cells with ATF- or ScFvEGFR-IO nanoparticles significantly inhibited proliferation of the tumor cells (FIG. 9A). Induction of cell death was also found after treatment, especially in ScFvEGFR treated cells (FIG. 9B). Therefore, ATF and ScFvEGFR have potential to serve as tumor targeting peptides as well as therapeutic reagents.

In Vivo Imaging of Orthotopic Human Pancreatic Tumor Xenografts after Systemic Delivery of ATF-IO or ScFvEGFR-IO Nanoparticles:

To determine MRI specificity and tissue distribution of the targeted IO nanoparticles, a human pancreatic tumor model was established in nude mice. MR images of the tumor bearing mice before and after administration of different IO nanoparticles via. the tail vein of each mouse. Post contrast MRI scans were performed at different time points from about 5 minutes to 30 hours.

Figure 10:
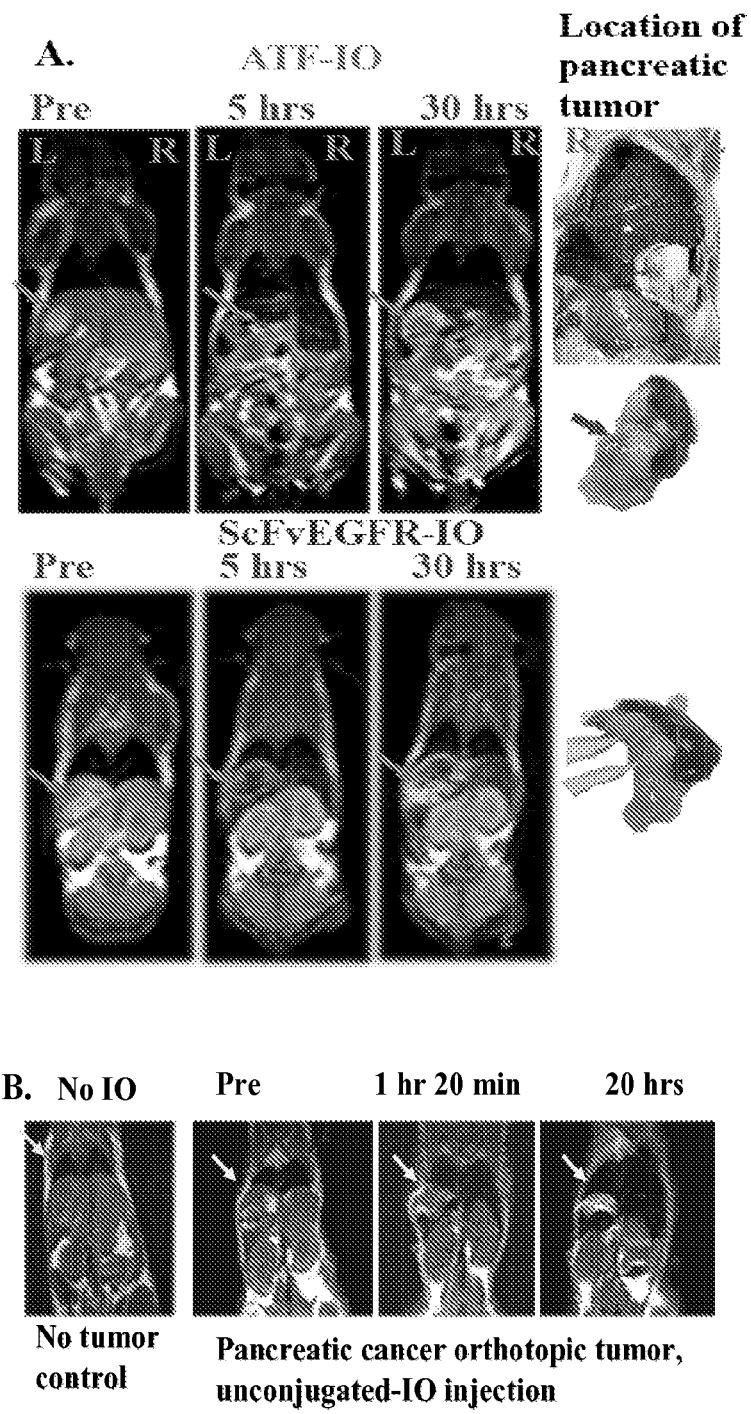
FIG. 10 shows according to one embodiment of the present invention. MRI detection of pancreatic cancer lesions xenografted inside pancreas of nude mice using ATF-OI or ScFvEGFR-IO nanoparticles. A. MRI images of the tumor-bearing mice after ATF or ScFvEGFR-IO particle injection. Arrows indicate the tumor areas. Images showing were representative images from one of five mice in each group. B. MRI image of a normal mouse did not show bright signal in pancreatic areas. Moreover, T2 effect was not detected in the tumor-bearing mice after injection of unconjugated-IO particles.

MRI scan of animals bearing orthotopic pancreatic tumors showed bright signals in the tumor areas in T1 weighted imaging before the IO nanoparticle injection (FIG. 10A, Pre). However, about 5 hours after systemic delivery of ATF- or ScFvEGFR-IO nanoparticles, a significant signal drop in those areas was observed (FIG. 10A, 5 hrs), suggesting a T2 shortening effect from the accumulation of the targeted-IO nanoparticles in orthotopic pancreatic cancers. As expected, a strong T2 effect was also observed in liver and spleen of the mice due to high liver and spleen uptake of IO reported previously. At about 30 hours after administration of the contrast agent, signals in some tumor areas were slightly higher than that observed at 5 hours, suggesting dynamic changes in amount of the IO-nanoparticles in the tumors (FIG. 10A, 30 hrs).

In the postmortem examination of the mice after completion of MRI scans, it was found that the location of orthotopic pancreatic tumors observed in the mice correlates well with the tumor images obtained from MRI scan. For example, a tumor mass (5 mm) located inside pancreas and under the spleen (FIG. 10A) was found in a tumor-bearing mouse injected with ATF-IO. MRI scan also detected a similar sized area with hyper-intense signal in pre-contrast imaging but displaying hypo-intensity due to the strong T2 effect (FIG. 10A) introduced by the presence of IO. However, images from a tumor-bearing mouse injected with unconjugated IO nanoparticles did not show such significant T2 signal change in the tumor area (FIG. 10B).

Figure 11:
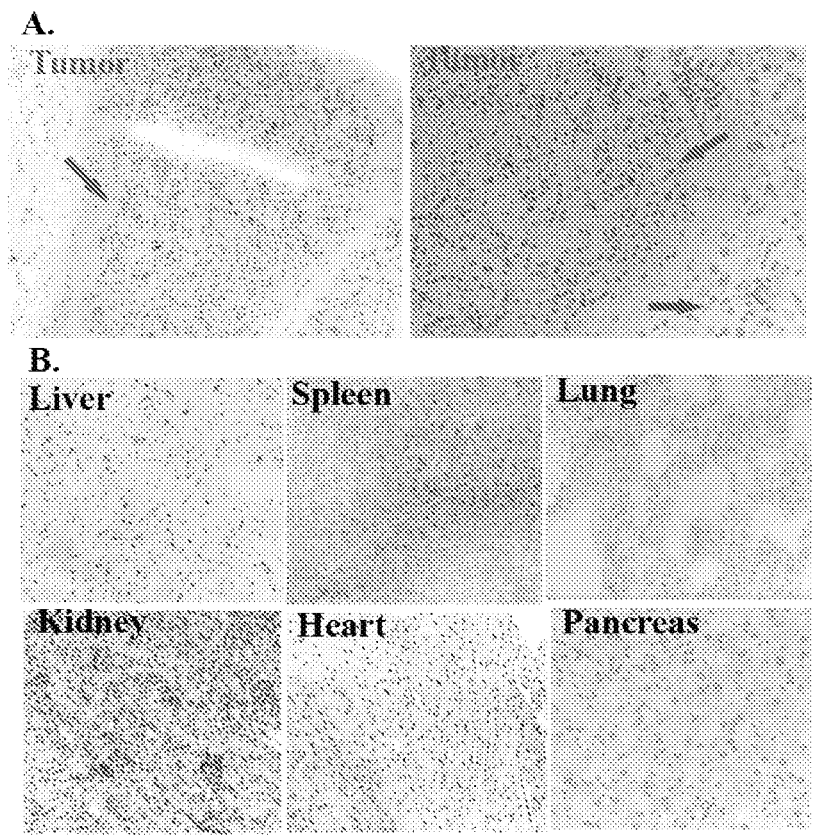
FIG. 11 shows images of tissue distribution of ATF-IO nanoparticles after the tail vein delivery. A. Selective accumulation of the IO particles in pancreatic tumor (red arrows) but not in normal pancreas adjacent to tumor areas (green arrow). B. In normal tissue, blue iron staining was detected in liver and spleen but not in normal pancreas, heart and kidney. A low level of blue staining was detected in lung. Red: counter staining with nuclear red. All tissues were collected from the same mouse 30 hrs after ATF-IO nanoparticle injection.

To determine the tissue distribution of the targeted-IO nanoparticles, tissues were collected from pancreatic tumors and several normal organs of a mouse injected with ATF-IO nanoparticles for about 30 hours. Frozen tissue sections from the tumor and normal organs were examined by Prussian blue staining. Interestingly, it is found a strong iron staining in pancreatic tumor lesions but not in surround normal pancreas (FIG. 11A). A high level of iron staining was also detected in liver and spleen. A low level of iron staining was seen in lung tissue. However, kidney, pancreas and heart tissues were consistently negative for the iron staining (FIG. 11B).

Thus, among other things, a novel approach is disclosed to conjugate targeting peptide ligands to IO nanoparticles. Using uPAR or EGFR-targeted IO nanoparticles, specific binding of the IO nanoparticles to human pancreatic tumor cells can be achieved. Systemic delivery of the targeted IO nanoparticles leads to accumulation of the targeted IO nanoparticles and produced significant MRI signal change in orthotopic pancreatic tumor lesions in nude mice as the result of strong T2 effect from IO nanoparticles. Since both EGFR and uPAR can be internalized by cells, this may facilitate the accumulation of IO nanoparticles in the tumor. Upregulation of uPAR in intra-tumoral fibroblasts and endothelial cells should lead the further increase of the concentration of the imaging probes in the tumor to improve the sensitivity of MRI-detection. Additionally, ability of ATF- and ScFvEGFR-IO nanoparticles to internalize into tumor cells may allow those nanoparticles as vehicles for delivering therapeutic reagents into tumor cells. Therefore, the results suggested that ATF-IO or ScFvEGFR-IO nanoparticles have great potential for target specific in vivo MR imaging and therapy of pancreatic cancer.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1]. Gao X, Cui Y, Levenson R M, Chung L W, Nie S. In vivo cancer targeting and imaging with semiconductor quantum dots. Nat Biotechnol 2004; 22:969-76.

[2]. Harisinghani M G, Barentsz J, Hahn P F, Deserno W M, Tabatabaei S, van de Kaa C H, de la Rosette J, Weissleder R. Noninvasive detection of clinically occult lymph-node metastases in prostate cancer. N Engl J Med 2003; 348: 2491-9.

[3]. Hood J D, Bednarski M, Frausto R, Guccione S, Reisfeld R A, Xiang R, Cheresh D A. Tumor regression by targeted gene delivery to the neovasculature. Science 2002; 296: 2404-7.

[4]. Kumar N A, Schnall M D. MR imaging: its current and potential utility in the diagnosis and management of breast cancer. Magn Reson Imaging Clin N Am 2000; 8:715-28.

[5]. Bombardieri E, Crippa F. PET imaging in breast cancer. Q J Nucl Med 2001; 45:245-56.

[6]. Romer J, Nielsen B S, Ploug M. The urokinase receptor as a potential target in cancer therapy. Curr Pharm Des 2004; 10:2359-76.

[7]. Artemov D, Mori N, Ravi R, Bhujwalla Z M. Magnetic resonance molecular imaging of the HER-2/neu receptor. Cancer Res 2003; 63:2723-7.

[8]. Bander N H, Trabulsi E J, Kostakoglu L, Yao D, Vallabhajosula S, Smith-Jones P, Joyce M A, Milowsky M, Nanus D M, Goldsmith S J. Targeting metastatic prostate cancer with radiolabeled monoclonal antibody J591 to the extracellular domain of prostate specific membrane antigen. J Urol 2003; 170:1717-21.

[9]. Moon W K, Lin Y, O'Loughlin T, Tang Y, Kim D E, Weissleder R, Tung C H. Enhanced tumor detection using a folate receptor-targeted near-infrared fluorochrome conjugate. Bioconjug Chem 2003; 14:539-45.

[10]. Mahmood U, Weissleder R. Near-infrared optical imaging of proteases in cancer. Mol Cancer Ther 2003; 2:489-96.

[11]. Schimer M, Menrad A, Stephens A, Frenzel T, Hauff P, Licha K. Molecular imaging of tumor angiogenesis. Ann N.Y. Acad Sci 2004; 1014:67-75.

[12]. Brigger I, Dubernet C, Couvreur P. Nanoparticles in cancer therapy and diagnosis. Adv Drug Deliv Rev 2002; 54:631-51.

[13]. Brannon-Peppas L, Blanchette J O. Nanoparticle and targeted systems for cancer therapy. Adv Drug Deliv Rev 2004; 56:1649-59.

[14]. Hallahan D, Geng L, Qu S, Scarfone C, Giorgio T, Donnelly E, Gao X, Clanton J. Integrin-mediated targeting of drug delivery to irradiated tumor blood vessels. Cancer Cell 2003; 3:63-74.

[15]. Jain R K. Delivery of molecular and cellular medicine to solid tumors. Adv Drug Deliv Rev 1997; 26:71-90.

[16]. Padera T P, Stoll B R, Tooredman J B, Capen D, di Tomaso E, Jain R K. Pathology: cancer cells compress intratumour vessels. Nature 2004; 427:695.

[17]. Jain R K. Transport of molecules, particles, and cells in solid tumors. Annu Rev Biomed Eng 1999; 1:241-63.

[18]. Hanahan D, Weinberg R A. The hallmarks of cancer. Cell 2000; 100:57-70.

[19]. Behrendt N. The urokinase receptor (uPAR) and the uPAR-associated protein (uPARAP/Endo180): membrane proteins engaged in matrix turnover during tissue remodeling. Biol Chem 2004; 385:103-36.

[20]. Rabbani S A, Mazar A P. The role of the plasminogen activation system in angiogenesis and metastasis. Surg Oncol Clin N Am 2001; 10:393-415, x.

[21]. Liu D, Aguirre Ghiso J, Estrada Y, Ossowski L. EGFR is a transducer of the urokinase receptor initiated signal that is required for in vivo growth of a human carcinoma. Cancer Cell 2002; 1:445-57.

[22]. Carriero M V, Del Vecchio S, Capozzoli M, Franco P, Fontana L, Zannetti A, Botti G, D'Aiuto G, Salvatore M, Stoppelli M P. Urokinase receptor interacts with alpha(v) beta5 vitronectin receptor, promoting urokinase-dependent cell migration in breast cancer. Cancer Res 1999; 59:5307-14.

[23]. Hemsen A, Riethdorf L, Brunner N, Berger J, Ebel S, Thomssen C, Janicke F, Pantel K. Comparative evaluation of urokinase-type plasminogen activator receptor expression in primary breast carcinomas and on metastatic tumor cells. Int J Cancer 2003; 107:903-9.

[24]. Meijer-van Gelder M E, Look M P, Peters H A, Schmitt M, Brunner N, Harbeck N, Klijn J G, Foekens J A. Urokinase-type plasminogen activator system in breast cancer: association with tamoxifen therapy in recurrent disease. Cancer Res 2004; 64:4563-8.

[25]. Solberg H, Ploug M, Hoyer-Hansen G, Nielsen B S, Lund L R. The murine receptor for urokinase-type plasminogen activator is primarily expressed in tissues actively undergoing remodeling. J Histochem Cytochem 2001; 49:237-46.

[26]. Dear A E, Medcalf R L. The urokinase-type-plasminogen-activator receptor (CD87) is a pleiotropic molecule. Eur J Biochem 1998; 252:185-93.

[27]. Li H, Lu H, Griscelli F, Opolon P, Sun L Q, Ragot T, Legrand Y, Belin D, Soria J, Soria C, Perricaudet M, Yeh P. Adenovirus-mediated delivery of a uPA/uPAR antagonist suppresses angiogenesis-dependent tumor growth and dissemination in mice. Gene Ther 1998; 5:1105-13.

[28]. Ignar D M, Andrews J L, Witherspoon S M, Leray J D, Clay W C, Kilpatrick K, Onori J, Kost T, Emerson D L. Inhibition of establishment of primary and micrometastatic tumors by a urokinase plasminogen activator receptor antagonist. Clin Exp Metastasis 1998; 16:9-20.

[29]. Harris R C, Chung E, Coffey R J. EGF receptor ligands. Exp Cell Res 2003; 284:2-13.

[30]. Mendelsohn J. Targeting the epidermal growth factor receptor for cancer therapy. Clin Oncol 2002; 20:1 S-13S.

[31]. Arteaga C L, Baselga J. Tyrosine kinase inhibitors: why does the current process of clinical development not apply to them? Cancer Cell 2004; 5:525-31.

[32]. Dancey J E. Predictive factors for epidermal growth factor receptor inhibitors—the bull's-eye hits the arrow. Cancer Cell 2004; 5:411-5.

[33]. Arteaga C L, Truica C I. Challenges in the development of anti-epidermal growth factor receptor therapies in breast cancer. Semin Oncol 2004; 31:3-8.

[34]. Aziz S A, Pervez S, Khan S, Kayani N, Rahbar M H. Epidermal growth factor receptor (EGFR) as a prognostic marker: an immunohistochemical study on 315 consecutive breast carcinoma patients. J Pak Med Assoc 2002; 52:104-10.

[35]. Wikstrand C J, McLendon R E, Friedman A H, Bigner D D. Cell surface localization and density of the tumor-associated variant of the epidermal growth factor receptor, EGFRvIII. Cancer Res 1997; 57:4130-40.

[36]. Tsutsui S, Ohno S, Murakami S, Hachitanda Y, Oda S. Prognostic value of epidermal growth factor receptor (EGFR) and its relationship to the estrogen receptor status in 1029 patients with breast cancer. Breast Cancer Res Treat 2002; 71:67-75.

[37]. Nicholson R I, Gee J M, Harper M E. EGFR and cancer prognosis. Eur J Cancer 2001; 37 Suppl 4S9-15.

[38]. Albanell J, Codony J, Rovira A, Mellado B, Gascon P. Mechanism of action of anti-HER2 monoclonal antibodies: scientific update on trastuzumab and 2C4. Adv Exp Med Biol 2003; 532:253-68.

[39]. Solbach C, Roller M, Ahr A, Loibl S, Nicoletti M, Stegmueller M, Kreysch H G, Knecht R, Kaufmann M. Anti-epidermal growth factor receptor-antibody therapy for treatment of breast cancer. Int J Cancer 2002; 101:390-4.

[40]. Kim E S, Khuri F R, Herbst R S. Epidermal growth factor receptor biology (IMC-C225). Curr Opin Oncol 2001; 13:506-13.

[41]. Adams G P, Schier R, McCall A M, Simmons H H, Horak E M, Alpaugh R K, Marks J D, Weiner L M. High affinity restricts the localization and tumor penetration of single-chain fv antibody molecules. Cancer Res 2001; 61:4750-5.

[42]. Bruell D, Bruns C J, Yezhelyev M, Huhn M, Muller J, Ischenko I, Fischer R, Finnern R, Jauch K W, Barth S. Recombinant anti-EGFR immunotoxin 425(scFv)-ETA' demonstrates anti-tumor activity against disseminated human pancreatic cancer in nude mice. Int J Mol Med 2005; 15:305-13.

[43]. Jannot C B, Beerli R R, Mason S, Gullick W J, Hynes N E. Intracellular expression of a single-chain antibody directed to the EGFR leads to growth inhibition of tumor cells. Oncogene 1996; 13:275-82.

[44]. Shinkai M, Ito A. Functional magnetic particles for medical application. Adv Biochem Eng Biotechnol 2004; 91:191-220.

[45]. Bulte J W, Kraitchman D L. Iron oxide MR contrast agents for molecular and cellular imaging. NMR Biomed 2004; 17:484-99.

[46]. Akerman M E, Chan W C, Laakkonen P, Bhatia S N, Ruoslahti E. Nanocrystal targeting in vivo. Proc Natl Acad Sci USA 2002; 99:12617-21.

[47]. Rusckowski M, Qu T, Chang F, Hnatowich D J. Technetium-99m labeled epidermal growth factor-tumor imaging in mice. J Pept Res 1997; 50:393-401.

[48]. Gao X, Nie S. Quantum dot-encoded mesoporous beads with high brightness and uniformity: rapid readout using flow cytometry. Anal Chem 2004; 76:2406-10.

[49]. Bailey R E, Nie S. Alloyed semiconductor quantum dots: tuning the optical properties without changing the particle size. J Am Chem Soc 2003; 125:7100-6.

[50]. Kim S, Lim Y T, Soltesz E G, De Grand A M, Lee J, Nakayama A, Parker J A, Mihaljevic T, Laurence R G, Dor D M, Cohn L H, Bawendi M G, Frangioni J V. Near-infrared fluorescent type II quantum dots for sentinel lymph node mapping. Nat Biotechnol 2004; 22:93-7.

[51]. Chen X, Conti P S, Moats R A. In vivo near-infrared fluorescence imaging of integrin alphavbeta3 in brain tumor xenografts. Cancer Res 2004; 64:8009-14.

[52]. Law B, Curino A, Bugge T H, Weissleder R, Tung C H. Design, synthesis, and characterization of urokinase plasminogen-activator-sensitive near-infrared reporter. Chem Biol 2004; 11:99-106.

[53]. Soltesz E G, Kim S, Laurence R G, DeGrand A M, Parungo C P, Dor D M, Cohn L H, Bawendi M G, Frangioni J V, Mihaljevic T. Intraoperative sentinel lymph node mapping of the lung using near-infrared fluorescent quantum dots. Ann Thorac Surg 2005; 79:269-77; discussion 269-77.

[54]. Gupta A K, Gupta M. Synthesis and surface engineering of iron oxide nanoparticles for biomedical applications. Biomaterials 2005; 26:3995-4021.

[55]. Sundstrom J B, Mao H, Santoianni R, Villinger F, Little D M, Huynh T T, Mayne A E, Hao E, Ansari A A. Magnetic resonance imaging of activated proliferating rhesus macaque T cells labeled with superparamagnetic monocrystalline iron oxide nanoparticles. J Acquir Immune Defic Syndr 2004; 35:9-21.

[56]. Funovics M A, Kapeller B, Hoeller C, Su H S, Kunstfeld R, Puig S, Macfelda K. MR imaging of the her2/neu and 9.2.27 tumor antigens using immunospecific contrast agents. Magn Reson Imaging 2004; 22:843-50.

[57]. Josephson L, Kircher M F, Mahmood U, Tang Y, Weissleder R. Near-infrared fluorescent nanoparticles as combined MR/optical imaging probes. Bioconjug Chem 2002; 13:554-60.

[58]. Kobayashi H, Brechbiel M W. Dendrimer-based nanosized MRI contrast agents. Curr Pharm Biotechnol 2004; 5:539-49.

[59]. Artemov D, Mori N, Okollie B, Bhujwalla Z M. MR molecular imaging of the Her-2/neu receptor in breast cancer cells using targeted iron oxide nanoparticles. Magn Reson Med 2003; 49:403-8.

What is claimed is:

1. A nanostructure, comprising:
   a. a magnetic iron oxide nanoparticle;
   b. a hydrophobic protection structure including at least an amphiphilic copolymer, wherein the hydrophobic protection structure at least partially encapsulates the magnetic iron oxide nanoparticle; and
   c. at least one epidermal growth factor receptor (EGFR) antibody conjugated to the hydrophobic protection structure.

2. The nanostructure of claim 1, wherein the at least one EGFR antibody is labeled with a fluorescence dye.

3. The nanostructure of claim 2, wherein the fluorescence dye is a Cy5.5 or an ICG.

4. The nanostructure of claim 1, wherein the at least one EGFR antibody is a single chain antibody to the epidermal growth factor receptor (ScFvEGFR).

5. The nanostructure of claim 1, being capable of targeting to tumor cells expressing EGFR.

6. The nanostructure of claim 1, wherein the amphiphilic copolymer comprises an amphiphilic block copolymer, an amphiphilic random copolymer, an amphiphilic alternating copolymer, an amphiphilic periodic copolymer, or any combination thereof.

7. The nanostructure of claim 6, wherein the amphiphilic copolymer comprises an amphiphilic block copolymer selected from the group consisting of an amphiphilic diblock copolymer, a triblock copolymer, or any combination thereof.

8. The nanostructure of claim 7, wherein the amphiphilic block copolymer includes an ABC triblock structure having one or more grafted 8-carbon alkyl side chains.

9. The nanostructure of claim 8, wherein the ABC triblock structure includes a poly-butylacrylate segment, a poly-ethylacrylate segment, and a poly-methacrylic acid segment.

10. The nanostructure of claim 1, wherein the amphiphilic copolymer has a molecular weight of about 10,000 to 200,000.

11. The nanostructure of claim 1, wherein the magnetic iron oxide nanoparticle has a core size of about 1-50 nm.

12. The nanostructure of claim 1, further comprising a probe disposed on the hydrophobic protection structure, wherein the probe comprises an antibody, a polypeptide, a polynucleotide, a drug molecule, an inhibitor compound, or any combination thereof.

13. A pharmaceutical composition comprising the nanostructure of claim 1.

14. The pharmaceutical composition of claim 13, further comprising a probe releasably attached onto the nanostructure, wherein the probe comprises an antibody, a polypeptide, a polynucleotide, a drug molecule, an inhibitor compound, or any combination thereof.

15. A method for target imaging and/or therapy, comprising:
   introducing the nanostructure of claim 1 into a subject; and
   determining the presence of the target in the subject by detecting the nanostructure.

16. The method of claim 15, wherein the at least one EGFR antibody is labeled with a fluorescence dye.

17. The method of claim 15, wherein the nanostructure is visible in magnetic resonance imaging (MRI).

18. The method of claim 15, wherein the magnetic iron oxide nanoparticle has a core size of about 1-50 nm.

19. The method of claim 15, wherein the nanostructure further comprises a probe deposed on or encapsulated in the hydrophobic protection structure, and wherein the probe comprises an antibody, a polypeptide, a polynucleotide, a drug molecule, an inhibitor compound, or any combination thereof.

20. The method of claim 15, wherein the target is tumor cells expressing EGFR.

21. The method of claim 20, wherein the tumor cells is at least one of pancreatic cancer cells or breast cancer cells.

22. The method of claim 15, wherein the introducing step is performed by a subcutaneous injection or a systemic injection.

23. The method of claim 22, wherein when the introducing step is performed by a systemic injection, a plurality of the nanostructure is accumulated substantially in the target region of the subject.

24. The method of claim 15, wherein the determining step is performed in vivo.

25. The method of claim 15, wherein determining comprises acquiring an image of the target.

26. The method of claim 15, wherein the determining step includes a passive targeting process or an active targeting process.

27. The method of claim 15, wherein introducing the nanostructure into the subject causes selective accumulation of the nanostructure in a target region of the subject.

28. The method of claim 15, wherein determining the presence of the target in the subject comprises:
   acquiring at least one image of the target; and
   determining the presence of the target in the subject from the acquired at least one image of the target.

29. The method of claim 28, wherein acquiring at least one image of the target comprises acquiring at least one of an MRI image and a florescence image.

* * * * *